US012630944B2

(12) United States Patent
Allen et al.

(10) Patent No.: US 12,630,944 B2
(45) Date of Patent: May 19, 2026

(54) METHODS, COMPOSITIONS, AND KITS FOR INHIBITING FORMATION OF ADAPTER DIMERS

(71) Applicant: Revvity Health Sciences, Inc., Waltham, MA (US)

(72) Inventors: Kevin D. Allen, Austin, TX (US); Kerry Gunning, Austin, TX (US); Allyson LeBas, Austin, TX (US); Eric Castro, Austin, TX (US)

(73) Assignee: Revvity Health Sciences, Inc., Waltham, MA (US)

( * ) Notice: Subject to any disclaimer, the term of this patent is extended or adjusted under 35 U.S.C. 154(b) by 553 days.

(21) Appl. No.: 18/126,074

(22) Filed: Mar. 24, 2023

(65) Prior Publication Data

US 2023/0323341 A1     Oct. 12, 2023

Related U.S. Application Data

(60) Provisional application No. 63/323,778, filed on Mar. 25, 2022.

(51) Int. Cl.
*C40B 50/06*         (2006.01)
*C12N 15/10*         (2006.01)
(52) U.S. Cl.
CPC .......... *C40B 50/06* (2013.01); *C12N 15/1093* (2013.01)
(58) Field of Classification Search
None
See application file for complete search history.

(56) References Cited

U.S. PATENT DOCUMENTS 9,650,667 B2    5/2017  McReynolds et al.
9,708,658 B2    7/2017  Richard
        (Continued)

FOREIGN PATENT DOCUMENTS

WO    2012/033687 A1    3/2012
WO    2016/164866 A1    10/2016
        (Continued)

OTHER PUBLICATIONS

International Search Report and Written Opinion for PCT/US2023/016295, dated Jul. 27, 2023.
        (Continued)

*Primary Examiner* — Christian C Boesen
(74) *Attorney, Agent, or Firm* — Julie K. Staple; Fishman Stewart PLLC

(57)         ABSTRACT

Methods of reducing adapter-dimers in a sequencing library are provided according to aspects of the present disclosure, including: hybridizing excess 3' adapters to blocker oligonucleotides forming a hybridized complex, such that the excess 3' adapters are unavailable to form adapter-dimers, the hybridized complex including: a first blocker oligonucleotide 3' terminus adjacent to an adenylated nucleotide at 5' terminus of a first unligated 3' adapter and a second blocker oligonucleotide 3' terminus adjacent to an adenylated nucleotide at 5' terminus of a second unligated 3' adapter, wherein the first blocker oligonucleotide has a 5' portion complementary to and hybridized to the first unligated 3' adapter, the second blocker oligonucleotide has a 5' portion complementary to and hybridized to the second unligated 3' adapter, and the first blocker oligonucleotide has a 3' portion complementary to, and hybridized to, a 3' portion of the second blocker oligonucleotide.

14 Claims, 8 Drawing Sheets

Specification includes a Sequence Listing.

Single adapter System
(non-palindromic)

(56) References Cited

U.S. PATENT DOCUMENTS

| | | |
|---|---|---|
| 9,790,540 B2 | 10/2017 | Vaidyanathan et al. |
| 9,970,048 B2 | 5/2018 | Gu et al. |
| 10,597,706 B2 | 3/2020 | Toloue et al. |
| 2013/0157869 A1* | 6/2013 | McReynolds ........ C12Q 1/6869 |
| | | 506/9 |
| 2013/0330778 A1 | 12/2013 | Zeiner et al. |
| 2016/0024566 A1 | 1/2016 | Dong et al. |

FOREIGN PATENT DOCUMENTS

| | | |
|---|---|---|
| WO | 2019/005978 A2 | 1/2019 |
| WO | 2020/247950 A1 | 12/2020 |
| WO | 2021/232023 A2 | 11/2021 |
| WO | 2022/046797 A1 | 3/2022 |

OTHER PUBLICATIONS

Kawano, M. et al., Reduction of non-insert sequence reads by dimer eliminator LNA oligonucleotide for small RNA deep sequencing, BioTechniques, 49:751-754, Oct. 2010.

* cited by examiner

SEQUENCE LISTING

```
Sequence total quantity: 6
SEQ ID NO: 1           moltype = DNA  length = 21
FEATURE                Location/Qualifiers
source                 1..21
                       mol_type = other DNA
                       organism = synthetic construct
modified_base          17
                       mod_base = OTHER
                       note = isodG
modified_base          18
                       mod_base = OTHER
                       note = isodC
modified_base          19
                       mod_base = OTHER
                       note = isodG
modified_base          20
                       mod_base = OTHER
                       note = isodC
SEQUENCE: 1
cacccgagaa ttccacgcgc g                                      21

SEQ ID NO: 2           moltype = DNA  length = 24
FEATURE                Location/Qualifiers
source                 1..24
                       mol_type = other DNA
                       organism = synthetic construct
modified_base          2
                       mod_base = OTHER
                       note = locked nucleic acid nucleotide
modified_base          3
                       mod_base = OTHER
                       note = locked nucleic acid nucleotide
modified_base          5
                       mod_base = OTHER
                       note = locked nucleic acid nucleotide
modified_base          7..9
                       mod_base = OTHER
                       note = locked nucleic acid nucleotide
modified_base          11..12
                       mod_base = OTHER
                       note = locked nucleic acid nucleotide
modified_base          14..15
                       mod_base = OTHER
                       note = locked nucleic acid nucleotide
modified_base          17..20
                       mod_base = OTHER
                       note = locked nucleic acid nucleotide
modified_base          22..24
                       mod_base = OTHER
                       note = locked nucleic acid nucleotide
SEQUENCE: 2
cgagaattcc agatcgtcgg actg                                   24
```

-continued

```
SEQ ID NO: 3          moltype = DNA   length = 21
FEATURE               Location/Qualifiers
source                1..21
                      mol_type = other DNA
                      organism = synthetic construct
SEQUENCE: 3
tggaattctc gggtgccaag g                                        21

SEQ ID NO: 4          moltype = RNA   length = 26
FEATURE               Location/Qualifiers
source                1..26
                      mol_type = other RNA
                      organism = synthetic construct
SEQUENCE: 4
gttcagagtt ctacagtccg acgatc                                   26

SEQ ID NO: 5          moltype = DNA   length = 21
FEATURE               Location/Qualifiers
source                1..21
                      mol_type = other DNA
                      organism = synthetic construct
SEQUENCE: 5
ccttggcacc cgagaattcc a                                        21

SEQ ID NO: 6          moltype = RNA   length = 29
FEATURE               Location/Qualifiers
source                1..29
                      mol_type = other RNA
                      organism = synthetic construct
SEQUENCE: 6
tctttcccta cacgacgctc ttccgatct                                29
```

METHODS, COMPOSITIONS, AND KITS FOR INHIBITING FORMATION OF ADAPTER DIMERS

REFERENCE TO RELATED APPLICATION

This application claims priority to U.S. Provisional Patent Application Ser. No. 63/323,778, filed Mar. 25, 2022, the entire content of which is incorporated herein by reference.

SEQUENCE LISTING

The instant application contains a Sequence Listing which has been submitted electronically as a file in XML format and is hereby incorporated by reference in its entirety. Said XML format file, created on Mar. 24, 2023, is named 16NEN27102PA.xml and is 12,732 bytes in size.

FIELD OF THE INVENTION

The present disclosure relates to methods, compositions, and kits for reducing adapter-dimers in a sequencing library.

BACKGROUND

Genetic analysis has become increasingly common and is useful in a wide variety of molecular biology applications. For example, genetic testing of individuals is particularly useful for early detection of genetic diseases and can play a role in selection of treatments for a particular disease or condition.

Massively parallel nucleic acid sequencing techniques play a key role in genetic analysis of target nucleic acids but produce less than optimal results when non-target nucleic acids are sequenced along with target nucleic acids.

Methods of target enrichment are often used to reduce contamination of sequencing results with non-target sequences in massively parallel nucleic acid sequencing techniques. One such enrichment method relies on hybridization capture of target nucleic acid sequencing library molecules.

However, sequencing libraries for massively parallel nucleic acid sequencing include adapter sequences attached to insert sequences in nucleic acid sequencing library molecules. Adapters include nucleic acid sequences with various functional properties, such as extension primer binding sites, one or more index sequences for sample identification, sequencing primer binding sites, and amplification primer binding sites. During the process of sequencing library production, adapters are ligated to insert sequences of interest. An undesirable by-product of adapter ligation to the insert sequences is that adapters can be ligated to each other, producing adapter-dimers. Even a small number of adapter-dimers can negatively affect sequencing quality since the adapter-dimers can be effectively amplified by amplification reactions intended to enrich for the insert sequences of interest.

Further, adapter-dimers can be retained by hybridization capture during enrichment steps, thereby capturing adapter-dimers and wasting reagents and time sequencing the adapter-dimers.

The expanding applications of massively parallel sequencing techniques and increasing need to multiplex larger numbers of individual libraries on a single run has resulted in the need to effectively inhibit formation of adapter-dimers, and remove those that do form.

There is a continuing need for compositions and methods for reducing adapter-dimers in sequencing libraries for massively parallel sequencing.

SUMMARY

Methods of reducing adapter-dimers in a sequencing library are provided according to aspects of the present disclosure which include: combining sample nucleic acids, each having a 5' end and a 3' end, with 3' adapters each having a 5' end portion at least 8 nucleotides in length and a 5' terminus which is an adenylated nucleotide, and a ligase, in a mixture under ligation reaction conditions, producing 1) first ligation products each including 3' end of a sample nucleic acid ligated to the 5' terminus of a 3' adapter, and 2) excess unligated, 3' adapters in the mixture; adding blocker oligonucleotides to the mixture, the blocker oligonucleotides including: a) a first blocker oligonucleotide including: i) a first blocker oligonucleotide 5' portion at least 8 nucleotides in length and ii) a first blocker oligonucleotide 3' portion at least 1 to 20 nucleotides in length and including a first oligonucleotide 3' terminus, wherein at least 1 of the 1 to 20 nucleotides is a non-naturally occurring nucleotide; and b) a second blocker oligonucleotide including: iii) a second oligonucleotide 5' portion at least 8 nucleotides in length and iv) a second blocker oligonucleotide 3' portion at least 1 to 20 nucleotides in length and including a second blocker oligonucleotide 3' terminus, wherein at least 1 of the 1 to 20 nucleotides is a non-naturally occurring nucleotide; wherein the first blocker oligonucleotide 3' portion and the second blocker oligonucleotide 3' portion are equal in length and complementary to each other; and wherein the first blocker oligonucleotide 5' portion and the second blocker oligonucleotide 5' portion are both complementary to 5' end portion of 3' adapters; and incubating the mixture under hybridization conditions, thereby hybridizing the first blocker oligonucleotide 3' portion with the second blocker oligonucleotide 3' portion, hybridizing the first blocker oligonucleotide 5' portion with the excess unligated 3' adapters, and thereby hybridizing the second blocker oligonucleotide 5' portion with the excess unligated 3' adapters, producing a hybridized complex wherein the first blocker oligonucleotide 3' terminus is adjacent to an adenylated 5' end nucleotide of a first unligated 3' adapter and the second blocker oligonucleotide 3' terminus is adjacent to an adenylated 5' end nucleotide of a second unligated 3' adapter, thereby reducing excess unligated 3' adapters in the mixture, producing a purified mixture.

According to aspects of the present disclosure, the first blocker oligonucleotide 3' terminus and the second blocker oligonucleotide 3' terminus are both capable of being ligated to the adenylated nucleotide at the 5' terminus of the excess unligated 3' adapters; and further including in a method of the present disclosure is ligating the first blocker oligonucleotide 3' terminus of the hybridized complex to the adjacent adenylated nucleotide at the 5' terminus of the first unligated 3' adapter and ligating the second blocker oligonucleotide 3' terminus of the hybridized complex to the adjacent adenylated nucleotide at the 5' terminus of the second unligated 3' adapter, producing ligated complex, thereby reducing excess unligated 3' adapters in the mixture, producing a purified mixture.

According to aspects of the present disclosure, 2, 3, 4, 5, 6, 7, 8, 9, 10, 11, 12, 13, 14, 15, 16, 17, 18, 19, or 20 of the at least 1 to 20 nucleotides of the first blocker oligonucleotide 3' portion are non-naturally occurring nucleotides and 2, 3, 4, 5, 6, 7, 8, 9, 10, 11, 12, 13, 14, 15, 16, 17, 18, 19, or 20 of the at least 1 to 20 nucleotides of the second blocker oligonucleotide 3' portion are non-naturally occurring nucleotides.

According to aspects of the present disclosure, the first blocker oligonucleotide 3' portion and the second blocker oligonucleotide 3' portion are each 2, 3, 4, 5, 6, 7, 8, 9, 10, 11, 12, 13, 14, 15, 16, 17, 18, 19, or 20 nucleotides in length, and the first blocker oligonucleotide 3' portion and the second blocker oligonucleotide 3' portion each comprise a palindromic nucleotide sequence, wherein the palindromic nucleotide sequence of the first blocker oligonucleotide 3' portion is identical to the palindromic nucleotide sequence of the second blocker oligonucleotide 3' portion.

According to aspects of the present disclosure, the first blocker oligonucleotide and the second blocker oligonucleotide each have a length in the range of 11 to 50 nucleotides.

According to aspects of the present disclosure, the first blocker oligonucleotide and the second blocker oligonucleotide have the same nucleotide sequence.

According to aspects of the present disclosure, methods of reducing adapter-dimers in a sequencing library further include adding a 5' adapter to the mixture, 5' adapter having a 3' terminus, wherein the first ligation products each comprise 3' end of a sample nucleic acid ligated to the 5' terminus of a 3' adapter, and 5' end of a sample nucleic acid ligated to the 3' terminus of a 5' adapter, thereby producing sequencing library molecules, the sequencing library molecules including a sample nucleic acid insert disposed between, and bonded to, a 5' adapter and a 3' adapter.

According to aspects of the present disclosure, methods of reducing adapter-dimers in a sequencing library further include adding a 5' adapter to the purified mixture; and incubating the purified mixture under ligation reaction conditions, thereby 1) ligating 5' adapter to the first ligation product, producing sequencing library molecules, the sequencing library molecules including a sample nucleic acid insert disposed between, and bonded to, a 5' adapter and a 3' adapter.

According to aspects of the present disclosure, methods of reducing adapter-dimers in a sequencing library are provided wherein excess unligated 3' adapters are reduced but not eliminated such that the ligating includes ligating 5' adapter to at least a portion of the excess unligated 3' adapter, producing adapter-dimers including a 5' adapter bonded to a 3' adapter at a 5' adapter-3' adapter interface. Thus, according to aspects of the present disclosure, methods of reducing adapter-dimers in a sequencing library are provided which further include inhibiting amplification of the adapter-dimers in an amplification reaction such that the sequencing library molecules are selectively enriched by the amplification reaction compared to the adapter-dimers. Inhibiting amplification of the adapter-dimers may include one or more of: removing at least some of the adapter-dimers prior to amplification; specific enzymatic cleavage of the adapter-dimers; CRISPR/Cas9-based cleavage of the adapter-dimers; gel purification to remove adapter-dimers; SPRI-bead based size selection to remove adapter-dimers; and adding an adapter-dimer blocker oligonucleotide to the mixture, the adapter-dimer blocker oligonucleotide effective to inhibit amplification of the adapter-dimers.

According to aspects of the present disclosure, methods of reducing adapter-dimers in a sequencing library are provided which include adding an adapter-dimer blocker oligonucleotide to the mixture, the adapter-dimer blocker oligonucleotide effective to inhibit amplification of the adapter-dimers, wherein the adapter-dimer blocker oligonucleotide is complementary to one or more adjacent portions of the adapter-dimers, the one or more adjacent portions including at least one nucleotide of 5' adapter at 5' adapter-3' adapter interface, and an adjacent portion of the 3' adapter including an amplification primer binding site.

According to aspects of the present disclosure, methods of reducing adapter-dimers in a sequencing library are provided wherein the sample nucleic acids are, or include, RNA.

According to aspects of the present disclosure, methods of reducing adapter-dimers in a sequencing library are provided wherein the sample nucleic acids are, or include, RNA, and the methods include reverse transcribing the RNA, producing reverse transcribed sequencing library molecules.

According to aspects of the present disclosure, methods of reducing adapter-dimers in a sequencing library are provided which further include amplifying the sequencing library molecules or reverse transcribed sequencing library molecules.

According to aspects of the present disclosure, a pair of oligonucleotides for reducing adapter-dimers in a sequencing library is provided which includes a) a first blocker oligonucleotide including: i) a first blocker oligonucleotide 5' portion at least 8 nucleotides in length and ii) a first blocker oligonucleotide 3' portion at least 1 to 20 nucleotides in length and including a first oligonucleotide 3' terminus, wherein at least 1 of the 1 to 20 nucleotides is a non-naturally occurring nucleotide; and b) a second blocker oligonucleotide including: iii) a second oligonucleotide 5' portion at least 8 nucleotides in length and iv) a second blocker oligonucleotide 3' portion at least 1 to 20 nucleotides in length and including a second blocker oligonucleotide 3' terminus, wherein at least 1 of the 1 to 20 nucleotides is a non-naturally occurring nucleotide; wherein the first blocker oligonucleotide 3' portion and the second blocker oligonucleotide 3' portion are equal in length and complementary to each other; wherein the first blocker oligonucleotide 5' portion and the second blocker oligonucleotide 5' portion are both complementary to 5' end portion of 3' adapters.

According to aspects of the present disclosure, the first blocker oligonucleotide 3' terminus and the second blocker oligonucleotide 3' terminus are both capable of being ligated to the adenylated nucleotide at the 5' terminus of the excess unligated 3' adapters.

According to aspects of the present disclosure, the pair of blocker oligonucleotides for reducing adapter-dimers in a sequencing library is provided wherein 2, 3, 4, 5, 6, 7, 8, 9, 10, 11, 12, 13, 14, 15, 16, 17, 18, 19, or 20 of the at least 1 to 20 nucleotides of the first blocker oligonucleotide 3' portion are non-naturally occurring nucleotides and 2, 3, 4, 5, 6, 7, 8, 9, 10, 11, 12, 13, 14, 15, 16, 17, 18, 19, or 20 of the at least 1 to 20 nucleotides of the second blocker oligonucleotide 3' portion are non-naturally occurring nucleotides.

According to aspects of the present disclosure, the pair of blocker oligonucleotides for reducing adapter-dimers in a sequencing library is provided wherein when the first blocker oligonucleotide 3' portion and the second blocker oligonucleotide 3' portion are each 2, 3, 4, 5, 6, 7, 8, 9, 10, 11, 12, 13, 14, 15, 16, 17, 18, 19, or 20 nucleotides in length, the first blocker oligonucleotide 3' portion and the second blocker oligonucleotide 3' portion each comprise a palindromic nucleotide sequence, wherein the palindromic nucleotide sequence of the first blocker oligonucleotide 3' portion is identical to the palindromic nucleotide sequence of the second blocker oligonucleotide 3' portion.

According to aspects of the present disclosure, the pair of blocker oligonucleotides for reducing adapter-dimers in a sequencing library is provided wherein the first blocker oligonucleotide and the second blocker oligonucleotide each have a length in the range of about 11 to about 50 nucleotides.

According to aspects of the present disclosure, the pair of blocker oligonucleotides for reducing adapter-dimers in a sequencing library is provided wherein the first blocker oligonucleotide and the second blocker oligonucleotide have the same nucleotide sequence.

Kits for reducing adapter-dimers in a sequencing library are provided according to aspects of the present disclosure which include one or more pairs of blocker oligonucleotides for reducing adapter-dimers in a sequencing library According to aspects of the present disclosure, kits for reducing adapter-dimers in a sequencing library further include an adapter-dimer blocker oligonucleotide effective to block amplification of adapter-dimers.

According to aspects of the present disclosure, kits for reducing adapter-dimers in a sequencing library are provided wherein the adapter-dimer blocker oligonucleotide is complementary to one or more adjacent portions of the adapter-dimers, the one or more adjacent portions including at least one nucleotide of 5' adapter at 5' adapter-3' adapter interface, and an adjacent portion of 3' adapter including an amplification primer binding site.

BRIEF DESCRIPTION OF THE DRAWINGS

FIG. 1 includes numbering showing features of the hybridized complex including: first blocker oligonucleotide 20; 3' terminus of the first blocker oligonucleotide 28; 5' portion of the first blocker oligonucleotide 30; first blocker oligonucleotide 3' portion 35; second blocker; oligonucleotide 5' portion 55; second blocker oligonucleotide 40; 3' terminus of the second blocker oligonucleotide 48; second blocker oligonucleotide 3' portion 50; 3' adapter 60; and 5' adenylated end of 3' adapter 62.

FIG. 3 shows the proportion of a) desired RNA successfully incorporated into sequencing library molecules (dark gray); b) proportion of adapter dimers (canonical dimers) formed and incorporated into sequencing library molecules (medium gray); and c) proportion of other molecules incorporated into sequencing library molecules (light gray), in a method of reducing adapter-dimers in a sequencing library using: #1) no method for blocking formation of adapter dimers; #2) a method including use of one or more blocker oligonucleotides according to aspects of the present disclosure; 3 #) a method including removing at least some adapter-dimers prior to amplification; or #4) a method including use of one or more blocker oligonucleotides according to aspects of the present disclosure and further including removing at least some adapter-dimers prior to amplification.

In FIG. 4 the light gray bars, 1, represent data obtained using a method including use of one or more blocker oligonucleotides according to aspects of the present disclosure and the dark gray bars, 2, represent data obtained using a conventional method.

DETAILED DESCRIPTION

Figure 1:
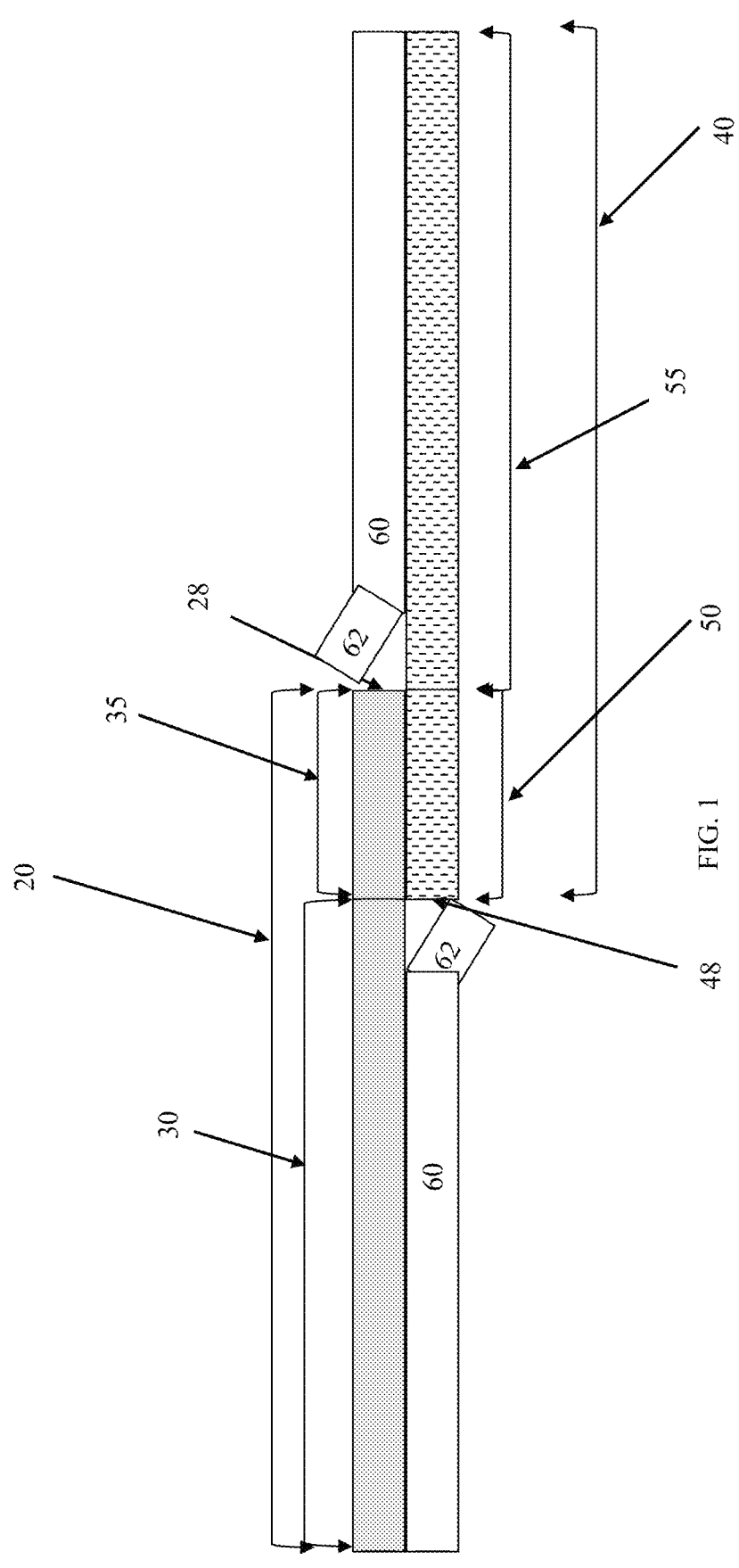
FIG. 1 is a diagrammatic illustration of a hybridized complex including blocker oligonucleotides and 3' adapters according to aspects of the present disclosure.
Figure 2A:
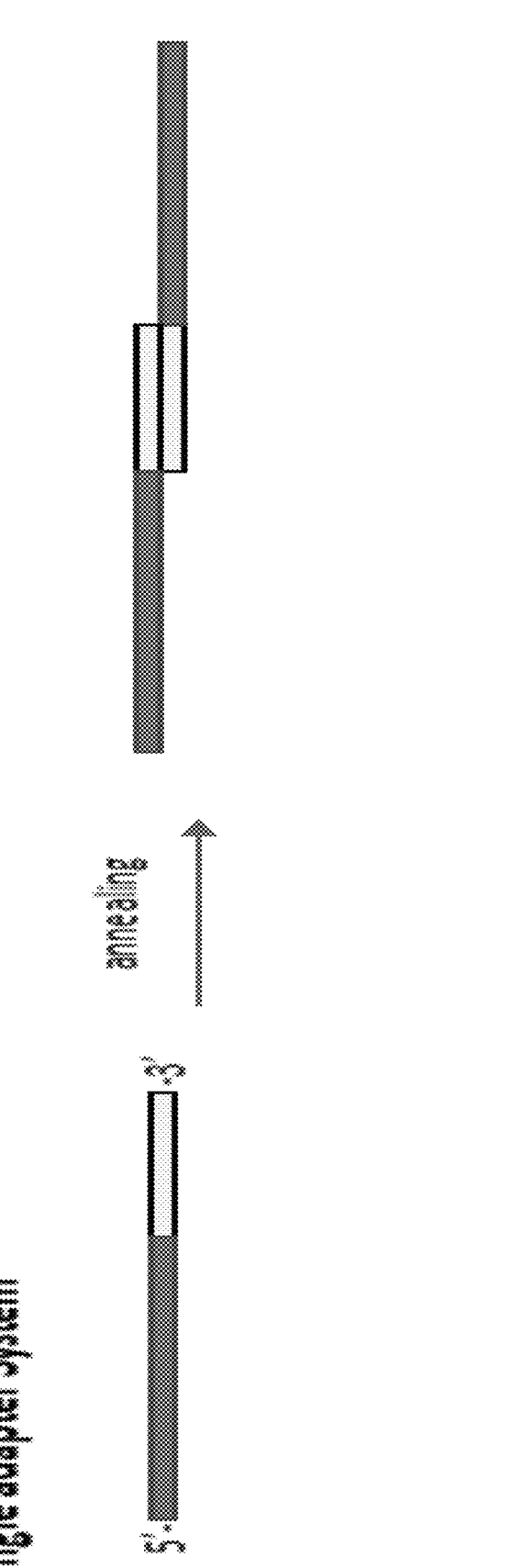
FIG. 2A is a schematic diagram showing a "single adapter system" in which the blocking oligonucleotides have the same sequence, include a blocker oligonucleotide 5' portion (dark gray) and include a palindromic blocker oligonucleotide 3' portion (light gray), such that the palindromic blocker oligonucleotide 3' portions are complementary and anneal as shown; A "single adapter system" is used, for example, in methods of sequencing library generation in which a single type of adapter is included.
Figure 2B:
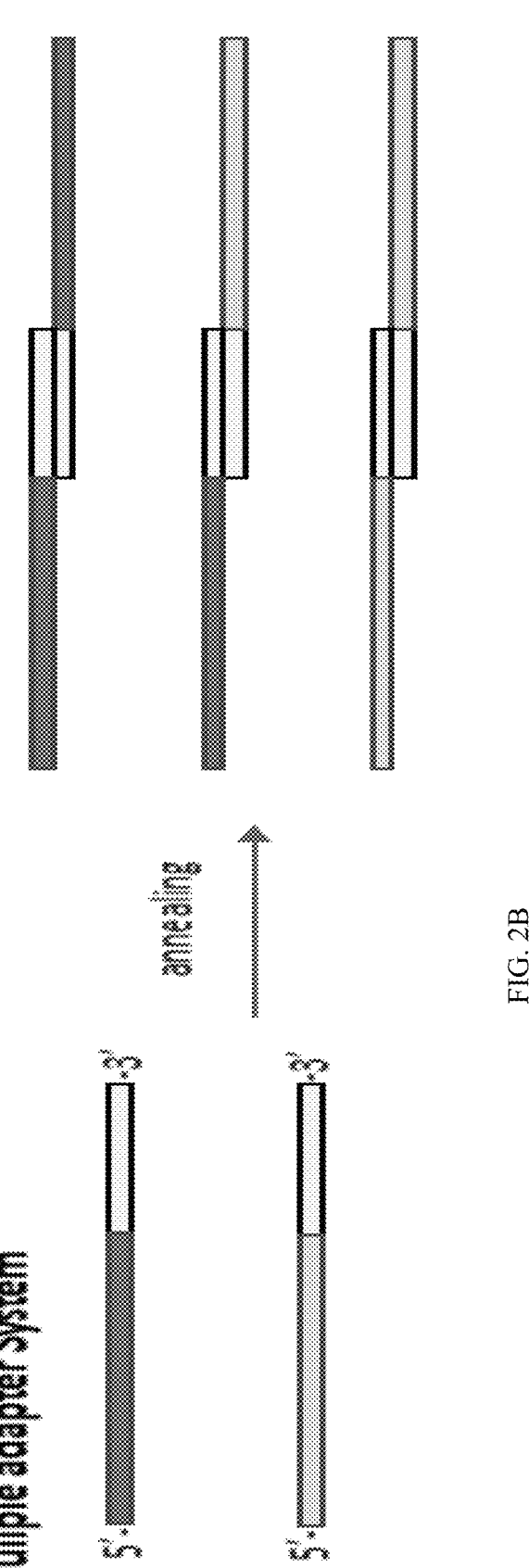
FIG. 2B is a schematic diagram showing a "multiple adapter system" including at least two types of blocking oligonucleotides, in which the different types of blocking oligonucleotides have different sequences, including different blocker oligonucleotide 5' portions (dark gray, top left; and medium gray, bottom left) and include identical palindromic blocker oligonucleotide 3' portions (light gray), such that the palindromic blocker oligonucleotide 3' portions are complementary and anneal as shown; A "multiple adapter system" is used, for example, in methods of sequencing library generation in which multiple types of adapter are included, e.g. each adapter including a different index sequence.
Figure 2C:
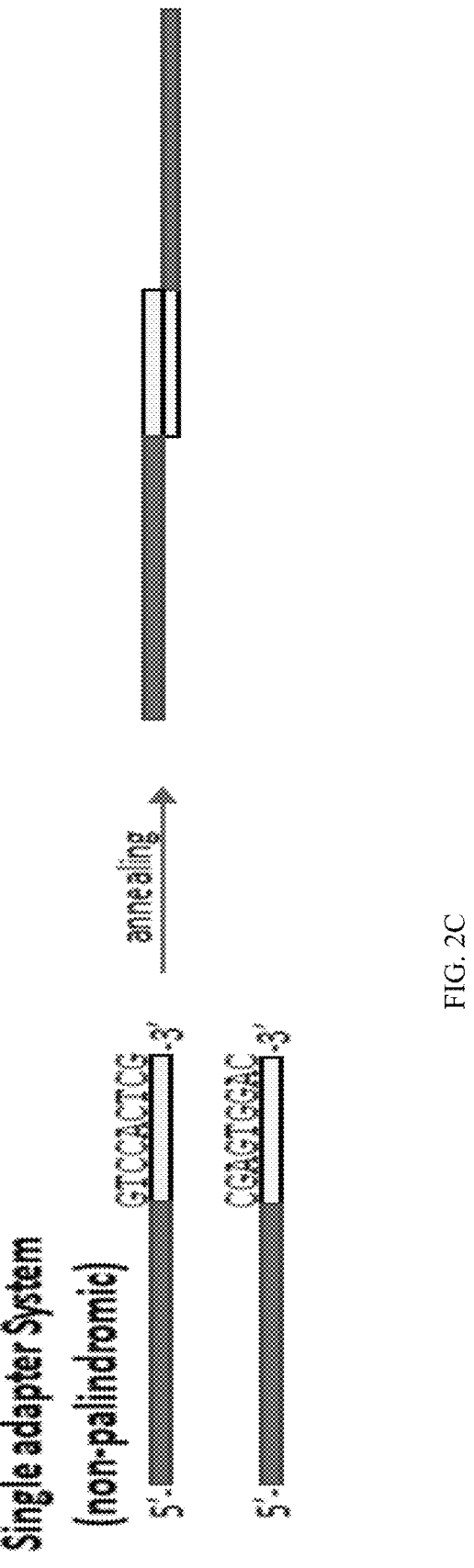
FIG. 2C is a schematic diagram showing a "single adapter system" including at least two types of blocking oligonucleotides, in which the different types of blocking oligonucleotides have different sequences, including identical blocker oligonucleotide 5' portions (dark gray) and include different non-palindromic blocker oligonucleotide 3' portions (light gray, top; stippled gray, bottom), such that the non-palindromic blocker oligonucleotide 3' portions are complementary and anneal as shown; A "single adapter system" is used, for example, in methods of sequencing library generation in which a single type of adapter is included.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The term "about," and grammatical equivalents thereof, as used herein in relation to a reference numerical value refers to the reference numerical value and numerical values within 10% of the reference numerical value, including numerical values which are plus or minus (+/−) 1%, +/−2%, +/−3%, +/−4%, +/−5%, +/−6%, +/−7%, +/−8%, +/−9%, or +/−10% of the reference numerical value. In the context of a stated range of reference numerical values, the term "about" and grammatical equivalents thereof, as used herein refers to a range which includes numerical values that are +/−1%, +/−2%, +/−3%, +/−4%, +/−5%, +/−6%, +/−7%, +/−8%, +/−9%, or +/−10% of the reference lower limit of the range of numerical values and numerical values that are +/−1%, +/−2%, +/−3%, +/−4%, +/−5%, +/−6%, +/−7%, +/−8%, +/−9%, or +/−10% of the reference upper limit of the range of numerical values. Further, unless otherwise specified, a listing of numerical values herein is understood to include all intermediate and fractional values of the listed numerical values, e.g., 50%, 60%, 75%, is understood to include 55%, 64.5%, and 74%.

The terms "first", "second", etc. may be used herein in reference to elements or combinations of elements, and these terms are used to designate such elements or combinations of elements without limitation as to whether the first element and second element are identical to each other or different.

Particular combinations of features are recited in the claims and/or disclosed in the specification, and these combinations of features are not intended to limit the disclosure of various aspects. All possible combinations of such features are not specifically recited in the claims and/or disclosed in the specification. Although each dependent claim listed below may directly depend on only one claim, the disclosure of various aspects includes each dependent claim in combination with every other claim in the claim set. As used herein, a phrase referring to "at least one of" a list of items refers to any combination of those items, including single members. As an example, "at least one of: a, b, or c" is intended to cover a alone; b alone; c alone, a and b, a, b, and c, b and c, a and c, as well as any combination with multiples of the same element, such as a and a; a, a, and a; a, a, and b; a, a, and c; a, b, and b; a, c, and c; and any other combination or ordering of a, b, and c).

Methods of reducing adapter-dimers in a sequencing library are provided according to aspects of the present disclosure, which include: hybridizing excess 3' adapters to blocker oligonucleotides to form a hybridization complex, such that the excess 3' adapters are unavailable to form adapter-dimers, wherein hybridization complex includes a first blocker oligonucleotide which has a 5' portion complementary to and hybridized to a first unligated 3' adapter, a second blocker oligonucleotide which has a 5' portion complementary to and hybridized to a second unligated 3' adapter, and wherein the first blocker oligonucleotide has a 3' portion complementary to, and hybridized to, a 3' portion of the second blocker oligonucleotide.

Optionally, 3' adapters are covalently bonded to the blocker oligonucleotides in the hybridization complex by ligation thereby forming a ligated complex wherein a first blocker oligonucleotide 3' terminus is ligated to an adjacent adenylated nucleotide at the 5' terminus of a first unligated 3' adapter and a second blocker oligonucleotide 3' terminus is ligated to an adjacent adenylated nucleotide at the 5' terminus of a second unligated 3' adapter, wherein the first blocker oligonucleotide which has a 5' portion complementary to and hybridized to a first unligated 3' adapter, a second blocker oligonucleotide which has a 5' portion complementary to and hybridized to a second unligated 3' adapter, and wherein the first blocker oligonucleotide has a 3' portion complementary to, and hybridized to, a 3' portion of the second blocker oligonucleotide.

The terms "blocker oligonucleotide" and "oligonucleotide blocker" as used interchangeably herein refer to a synthetic oligonucleotide which includes i) a blocker oligonucleotide 5' portion at least 8 nucleotides in length adjacent a 5' terminus, and ii) a blocker oligonucleotide 3' portion at least 1 to 20 nucleotides in length, adjacent a 3' terminus. According to aspects of the present disclosure, a blocker oligonucleotide has a total length in the range of about 9 nucleotides to about 50 nucleotides. According to aspects of the present disclosure, a blocker oligonucleotide has a total length of about 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, or about 50 nucleotides, and may be shorter, or longer.

According to aspects of the present disclosure, 2, 3, 4, 5, 6, 7, 8, 9, 10, 11, 12, 13, 14, 15, 16, 17, 18, 19, or 20 of the at least 1 to 20 nucleotides of the blocker oligonucleotide 3' portion are non-naturally occurring nucleotides.

According to aspects of the present disclosure, 2, 3, 4, 5, 6, 7, 8, 9, 10, 11, 12, 13, 14, 15, 16, 17, 18, 19, or 20 of the at least 1 to 20 nucleotides of the blocker oligonucleotide 3' portion are Tm increasing nucleotides and/or nucleotide analogs. According to aspects of the present disclosure, 2, 3, 4, 5, 6, 7, 8, 9, 10, 11, 12, 13, 14, 15, 16, 17, 18, 19, or 20 of the at least 1 to 20 nucleotides of the blocker oligonucleotide 3' portion are LNAs monomers, PNA monomers, BNA monomers, other $T_m$ increasing nucleotide analogs, or any two or more thereof. According to aspects of the present disclosure, 2, 3, 4, 5, 6, 7, 8, 9, 10, 11, 12, 13, 14, 15, 16, 17, 18, 19, or 20 of the at least 1 to 20 nucleotides of the blocker oligonucleotide 3' portion are LNA monomers.

According to aspects of the present disclosure, about 10%, 20%, 30%, 40%, 50%, 60%, 70%, 80%, 90% or more of the nucleotides of the blocker oligonucleotide 5' portion are non-naturally occurring nucleotides. According to aspects of the present disclosure, about 10%, 20%, 30%, 40%, 50%, 60%, 70%, 80%, 90% or more of the nucleotides of the blocker oligonucleotide 5' portion are Tm increasing nucleotides and/or nucleotide analogs. According to aspects of the present disclosure, about 10%, 20%, 30%, 40%, 50%, 60%, 70%, 80%, 90% or more of the nucleotides of the blocker oligonucleotide 5' portion are LNA monomers, PNA monomers, BNA monomers, other $T_m$ increasing nucleotide analogs, or any two or more thereof. According to aspects of the present disclosure, about 10%, 20%, 30%, 40%, 50%, 60%, 70%, 80%, 90% or more of the nucleotides of the blocker oligonucleotide 5' portion are LNA monomers.

According to aspects of the present disclosure, 3' portion of a blocker oligonucleotide is or includes a palindromic nucleotide sequence.

Oligonucleotides according to aspects of the present disclosure are generated synthetically using chemical synthetic and/or recombinant molecular biology techniques for example as detailed in Herdewijn, P. (Ed.), Oligonucleotide Synthesis: Methods and Applications, Methods in Molecular Biology, Humana Press, 2004.

An example blocker oligonucleotide is 5'-CACCCGAGAATTCCA—C/iisodG//iMe-isodC//iisodG//iMe-isodC/G-3' (SEQ ID NO:1).

FIG. 1 diagrammatically illustrates a first blocker oligonucleotide 20 and a second blocker oligonucleotide 40. The first blocker oligonucleotide 20 has a 5' portion 30 and a 3' portion 35. The 3' terminus of the first blocker oligonucleotide is shown at 28. The second blocker oligonucleotide has a 5' portion 55 and a 5' portion 50. The second blocker oligonucleotide 3' terminus is shown at 48. While the first and second blocker oligonucleotides are shown as equal in length to 3' adapters 60 and their ends 62, the first and second blocker oligonucleotides may be shorter or longer in length than 3' adapters 60 and their ends 62.

FIG. 1 shows a hybridized complex in which the first blocker oligonucleotide 3' portion 35 is hybridized with the second blocker oligonucleotide 3' portion 50. Further shown are 3' adapters 60 each having a 5' adenylated end 62. The 3' adapters 60 are shown hybridized to the 5' portion of the first blocker oligonucleotide 30 and 5' portion of the second blocker oligonucleotide. Also shown is an 5' adenylated end 62 of a 3' adapter adjacent the 3' terminus of the first blocker oligonucleotide 28 and an 5' adenylated end 62 of a 3' adapter adjacent the 3' terminus of the second blocker oligonucleotide 48.

Optionally, a ligation reaction is performed such that ligation of 5' adenylated end 62 of 3' adapter and the adjacent 3' terminus of the first blocker oligonucleotide 28 will occur in the presence of a ligase under ligation conditions; and ligation of 5' adenylated end 62 of the 3' adapter and the adjacent 3' terminus of the second blocker oligonucleotide 48 will occur in the presence of a ligase under ligation conditions, forming a ligated complex.

According to aspects of the present disclosure, the first and second blocker oligonucleotides are identical in sequence.

According to aspects of the present disclosure, the first and second blocker oligonucleotides are different in sequence.

The 5' portion of a blocker oligonucleotide of the present disclosure is complementary to 3' adapter such that 5' portion of a blocker oligonucleotide hybridizes to 3' adapter under hybridization conditions. The blocker oligonucleotide can be longer, shorter, or the same length as 3' adapter. The 5' portion of a blocker oligonucleotide can be completely complementary to 3' adapter, or can be 50%, 60%, 70%, 80%, 90%, or greater % complementary using hybridization conditions suitable for formation of a hybridization complex and subsequent ligation to form a ligated complex.

Methods, blocker oligonucleotides, and kits described herein may be used to generate sequencing libraries from sample nucleic acids derived from any of various sources. The sample nucleic acids, such as DNA or RNA, are typically present in a biological sample, which can be obtained from an individual, such as from a bodily sample, for example, blood, lymph, buccal swab, skin tissue, urine, saliva, tissue, sputum, peritoneal fluid, fecal material, gastric fluid, seminal fluid, cerebrospinal fluid, biopsy material, wound exudate, and the like, and cell lines derived therefrom. Prenatal biological sample nucleic acids can be obtained from amniotic fluid, products of conception, blastocysts and blastomeres, corionic villi, fetal cells, fetal DNA, and/or fetal RNA circulating in maternal blood. Sample nucleic acids also be obtained from in vitro sources such as cell lines.

Methods, blocker oligonucleotides, and kits described herein may be used to generate sequencing libraries from sample nucleic acids obtained from any of various organisms including, but not limited to, humans, non-human primates, rodents, rabbits, dogs, cats, horses, cattle, pigs, goats and sheep. Non-mammalian sources of sample nucleic acids can also be used, illustratively including fish and other aquatic organisms, birds, poultry, bacteria, viruses, plants, insects, reptiles, amphibians, fungi and mycobacteria. Thus, sample nucleic acids, such as sample DNA or sample RNA, may be obtained from any of these sources.

The sample nucleic acids, such as DNA or RNA, can be obtained from any source, including, but not limited to, a human, a non-human mammal, a vertebrate, an invertebrate, a microorganism, or a plant. The sample nucleic acids, such as DNA or RNA, can be obtained from one or more cells ex vivo or in vitro. For example, the sample nucleic acids, such as DNA or RNA, can be obtained from cultured cells, including, but not limited to, cell lines, primary cells or laboratory manipulated cells such as recombinant cells.

According to aspects of the present disclosure, the sample nucleic acids are "small RNA." The term "small RNA" as used herein refers to RNA which has a length in the range of about 10 nucleotides in length to about 300 nucleotides in length, such as RNA which has a length in the range of about 10 nucleotides in length to about 250 nucleotides in length, RNA which has a length in the range of about 10 nucleotides in length to about 200 nucleotides in length, RNA which has a length in the range of about 10 nucleotides in length to about 150 nucleotides in length, RNA which has a length in the range of about 10 nucleotides in length to about 100 nucleotides in length, RNA which has a length in the range of about 10 nucleotides in length to about 90 nucleotides in length, RNA which has a length in the range of about 10 nucleotides in length to about 80 nucleotides in length, RNA which has a length in the range of about 10 nucleotides in length to about 70 nucleotides in length, RNA which has a length in the range of about 10 nucleotides in length to about 60 nucleotides in length, RNA which has a length in the range of about 10 nucleotides in length to about 50 nucleotides in length, RNA which has a length in the range of about 10 nucleotides in length to about 40 nucleotides in length or RNA which has a length in the range of about 10 nucleotides in length to about 30 nucleotides in length. Small RNA may be any of: RNA fragments, rRNA, viral RNA, microRNA (miRNA), small interfering RNA (SiRNA), transfer RNA (tRNA), short hairpin RNA (shRNA), repeat-associated RNA (rasiRNA), small nucleolar RNA (snoRNA), Piwi-interacting RNA (piRNA), small cajal body RNA (scaRNA), heterochromatic siRNA (hc-siRNA), and trans-acting RNA (ta-siRNA).

The term "sequencing library" as used herein refers to a plurality of linear double-stranded DNA fragments which include an insert that is a sequencing target of interest derived from sample nucleic acids which may, or may not, be from the same source. The DNA fragments of a sequencing library further include functional elements flanking the insert which provide for, e.g. identification of the DNA fragments, such as barcode or index sequences, binding of an amplification primer, binding of a sequencing primer, or specific binding to a desired target, allowing for effective processing in a sequencing method, particularly massively parallel sequencing methods. A sequencing library may include inserts flanked by two adapters, a 5' adapter and a 3' adapter, wherein 5' adapter is covalently bonded to the 5' end of an insert, directly or indirectly, and a 3' adapter is covalently bonded to the 3' end of an insert, directly or indirectly. Indirect bonding of an adapter to an insert refers to a configuration in which another DNA sequence is disposed between the insert and an adapter.

The term "massively parallel sequencing," including "sequencing by synthesis," and also referred to as "next generation sequencing" and "high throughput sequencing," indicates a process of simultaneous or near-simultaneous sequencing of many nucleic acid sequencing library molecules, such as thousands of nucleic acid sequencing library molecules. Sets of oligonucleotide blockers provided according to aspects of the present disclosure are described herein with particular reference in some cases to Illumina Nextera and/or TruSeq platforms and configurations but are not limited thereto. Rather, the compositions and methods of the present disclosure may be used in any of various sequencing protocols and with various sequencing equipment, including, but not limited to, Ion Torrent systems.

The term "adapter" refers to a linear, single-stranded, double-stranded, or partially double-stranded, DNA fragment which includes functional elements which provide for, e.g. identification of the DNA fragments, amplification, or specific binding to a desired target, allowing for effective processing in a sequencing method. Adapters include one or more functional elements, such as a sequencing primer-binding sequence (also called a sequencing primer-binding site), an extension primer-binding sequence (also called an extension primer-binding site), and an index sequence (also called a barcode sequence or unique molecular identifier, UMI). The term "5' adapter" refers to an adapter covalently bonded to, or intended to be covalently bonded to, the 5' end of an insert, directly or indirectly. The term "3' adapter" refers to an adapter covalently bonded to, or intended to be covalently bonded to, 3' end of an insert, directly or indirectly. An adapter is typically about 10 to 150 nucleotides in length, such as about 10 to 25, 15 to 30, 25 to 40, 30 to 50, 45 to 75, 50 to 100, 90 to 125, or 120 to 150. It is noted that the term "adapter" is alternatively spelled "adaptor."

According to aspects of the present disclosure, 3' adapter is 5' adenylated at 5' end of 3' adapter to facilitate ligation of 3' adapter to the sample nucleic acids and to the blocker oligonucleotide(s).

According to aspects of the present disclosure, 5' adenylated 3' adapter included in methods, compositions, and/or kits is blocked on 3' end, such as by a 2',3'-dideoxy-nucleotide or 3' (C3) propyl spacer.

The term "end" as used herein in reference to a nucleic acid molecule refers to the end of a linear nucleic acid molecule and is used interchangeably herein with the term "terminus" or grammatical appropriate variations such as "termini." The term "end portion" as used herein in reference to a nucleic acid molecule refers to a nucleic acid sequence encompassing an end of the nucleic acid molecule and an adjacent contiguous nucleic acid sequence but not the entire length of the nucleic acid sequence of the nucleic acid molecule. According to aspects of the present disclosure, an "end portion" of a nucleic acid molecule refers to a nucleic acid sequence encompassing an end of the nucleic acid molecule and an adjacent contiguous nucleic acid sequence which makes up about half or less of the length of the entire nucleic acid sequence of the nucleic acid molecule.

The term "adapter-dimer" refers to an undesirable byproduct formed when ligating a 5' adapter and a 3' adapter to the 5' terminus and 3' terminus of sample nucleic acids in a process of generating a sequencing library. Specifically, an adapter-dimer is a ligation product of a 5' adenylated terminus of a 3' adapter and a 3' terminus of a 5' adapter. Adapter-dimers are undesirable in a process of generating a sequencing library since they may be amplified and compete with the sequencing library molecules in aspects of a process of generating a sequencing library, such as competing for binding sites in the flow cell, significantly lowering sequencing quality.

The term "ligation" as used herein refers to covalent bonding of two linear nucleic acid molecules to form a longer, linear nucleic acid molecule, mediated by a ligase enzyme.

The terms "ligase enzyme" and "ligase" are used interchangeably herein to refer to an enzyme capable of covalently bonding two adjacent nucleic acids forming a linkage between the two nucleic acids, such as a phosphodiester bond, or, depending on the identity of the terminal nucleotide, modified covalent bond such as, but not limited to, a phosphorothioate bond, or phosphoamidate bond. Ligase enzymes include, but are not limited to, T7 ligase, T4 ligase, *E. coli* ligase, and Taq ligase. Ligase enzymes include ATP-dependent ligases, NAD+-dependent ligases, and include DNA ligases and RNA ligases, such as those which are members of Enzyme Class EC 6.5 defined by the International Union of Biochemistry and Molecular Biology, including, but not limited to, EC 6.5.1.1 (ATP-dependent ligases), EC 6.5.1.2 (NAD+-dependent ligases), EC 6.5.1.3 (RNA ligases), EC 6.5.1.6 DNA ligase (ATP or NAD+), EC 6.5.1.7 DNA ligase (ATP, ADP or GTP), and EC 6.5.1.8 3'-phosphate/5'-hydroxy nucleic acid ligase.

Conditions for use of a ligase enzyme are well-known.

Nucleotides, nucleotide analogs, and non-naturally occurring nucleotides

The term "nucleotide" refers to a molecule including a nucleobase, sugar, and phosphate. Nucleotides are the monomeric units of a nucleic acid sequence, e.g. a DNA or RNA sequence. The term nucleotide includes ribonucleoside triphosphates, such as ATP, TTP, UTP, CTP, and GTP, and deoxyribonucleoside triphosphates, such as dATP, dCTP, dUTP, dGTP, and dTTP. Nucleotides are commonly referred to as A, T, G, C, or U as an abbreviation, in reference to the nucleobase, see Table I.

Standard IUPAC nucleotide codes are used herein as shown in Table I.

TABLE I

| Symbol | Description | Bases represented | | | | Complement |
| --- | --- | --- | --- | --- | --- | --- |
| A | Adenine | A | | | | T |
| C | Cytosine | | C | | | G |
| G | Guanine | | | G | | C |
| T | Thymine | | | | T | A |
| U | Uracil | | | | U | A |
| W | Weak | A | | | T | W |
| S | Strong | | C | G | | S |
| M | aMino | A | C | | | K |
| K | Keto | | | G | T | M |
| R | puRine | A | | G | | Y |
| Y | pYrimidine | | C | | T | R |
| B | not A | | C | G | T | V |
| D | not C | A | | G | T | H |
| H | not G | A | C | | T | D |
| V | not T | A | C | G | | B |
| N | any Nucleotide (not a gap) | A | C | G | T/U | N |

The terms "nucleic acid," "nucleotide sequence," and "nucleic acid sequence" refer to RNA, DNA, or RNA/DNA molecules having more than one nucleotide and/or nucleotide analog in any form including linear, single-stranded, double-stranded, oligonucleotide, or polynucleotide.

The term "nucleotide analog" refers to a modified or non-naturally occurring nucleotide, particularly nucleotide analogs which can be polymerized, with naturally occurring nucleotides and/or non-naturally occurring nucleotides, by template-directed nucleic acid polymerization, or non-template-directed nucleic acid polymerization, catalyzed by a nucleic acid polymerase. The term "nucleotide analog" refers to a nucleotide which contains one or more modifications to the base moiety and/or the sugar moiety, and/or the phosphate moiety which modifies at least one aspect of the chemical properties of the nucleotide analog compared to a reference standard nucleotide, while retaining other properties which allow the nucleotide analog to perform its intended function. Nucleotide analogs, and their incorporation into nucleic acids, are well known in the art and may be synthesized according to standard procedures and/or obtained commercially.

Particular nucleotide analogs are capable of Watson-Crick pairing via hydrogen bonds with a complementary nucleotide and illustratively include, but are not limited to, naturally-occurring and non-naturally-occurring nucleotides and analogs thereof including those containing an analog of a nucleotide base such as substituted purines or pyrimidines, deazapurines, methylpurines, methylpyrimidines, aminopurines, aminopyrimidines, thiopurines, thiopyrimidines, indoles, pyrroles, 7-deazaguanine, 7-deazaadenine, 7-methylguanine, hypoxanthine, pseudocytosine, pseudoisocytosine, isocytosine, isoguanine, 2-thiopyrimidines, 4-thiothymine, 6-thioguanine, nitropyrrole, nitroindole, and 4-methylindole. Nucleotide analogs include those containing an analog of a deoxyribose such as a substituted deoxyribose, a substituted or non-substituted arabinose, a substituted or non-substituted xylose, and a substituted or non-substituted pyranose. Nucleotide analogs include those containing an analog of a phosphate ester such as phosphorothioates, phosphorodithioates, phosphoroamidates, phosphoroselenoates, phosophoroanilothioates, phosphoroanilidates, phosphoroamidates, boronophosphates, phosphotriesters, and alkylphosphonates such as methylphosphonates.

Non-naturally occurring nucleotides, such as iso-dG and iso-dC, provide unique base-pairing with each other and no base-pairing (or hybridization) between the non-naturally occurring nucleotide and a naturally-occurring nucleotide base, e.g. iso-dG will not pair with dC and iso-dC will not pair with dG. The term "iso-dG" refers to isoguanosine. It is noted that the term "iisodG" is also used herein to refer to isoguanosine, e.g. as incorporated in a sequence. The term "iso-dC" refers to isocytosine. It is noted that the term "iMe-isodC" is also used herein to refer to isocytosine, e.g. as incorporated in a sequence.

The terms "$T_m$" and "melting temperature" refer to a temperature at which 50% (half) of population of double-stranded nucleic acid molecules become separated, i.e. single stranded. Methods for calculating $T_m$ are well-known in the art.

The term "$T_m$ increasing nucleotide analog" refers to a nucleotide analog that increases the melting temperature ($T_m$) of a double-stranded oligonucleotide that includes the nucleotide analog compared to the same double-stranded oligonucleotide without the nucleotide analog. A $T_m$ increasing nucleotide analog may include a modified nucleobase, a modified sugar, a modified phosphate, or a combination of any two or more such modifications.

$T_m$ increasing nucleotide analogs include, but are not limited to, a locked nucleic acid (LNA) monomer, a peptide nucleic acid (PNA) monomer, and a bridged nucleic acid (BNA) monomer.

Any of various $T_m$ increasing nucleotide analogs can be used including, but not limited to, an LNA monomer, PNA monomer, BNA monomer, or any two or more thereof, according to aspects of the present disclosure.

The term "LNA monomer" is used interchangeably herein with the terms "LNA nucleotide" and "LNA base" and refers to a nucleotide analog which includes a locked ribose due to presence of a covalent bond between the 2' oxygen and the 4' carbon of the ribose ring, that is, a 2'-0),4'-C-methylene-β-D-ribofuranosyl monomer which can be incorporated into an oligonucleotide, producing a "locked nucleic acid." LNA monomers have similar, or improved, Watson-Crick base pairing selectivity compared to conventional nucleotides. Examples of LNA monomers include, but are not limited to, adenine bicyclonucleoside monomers, cytosine bicyclonucleoside monomers, guanine bicyclonucleoside monomers, 5-methylcytosine bicyclonucleoside monomers, thymine bicyclonucleoside monomers, and uracil bicyclonucleoside monomers. The Tm of an oligonucleotide including one or more LNA monomers is increased due to enhanced properties such as enhanced base stacking. Typically, the Tm of a is increased by two to eight ° C. for each LNA monomer incorporated into an LNA oligonucleotide. LNA monomers may be synthesized using well-known methods or obtained commercially. The terms "locked nucleic acid" and LNA are used interchangeably herein to refer to an oligonucleotide which includes one or more LNA monomers. Any of various $T_m$ increasing nucleotide analogs can be used including, but not limited to, 5-methyl dC, 2, 6-diaminopurine, propynyl-deoxyuridine, 5-hydroxybutynl-2'-deoxyuridine, and combinations of any two or more thereof according to aspects of the present disclosure. Any Tm increasing nucleotide analogs, and/or derivatives thereof, can be included so long as the derivatives retain the function of increasing the melting temperature ($T_m$) of a double-stranded oligonucleotide that includes the nucleotide analog compared to the same double-stranded oligonucleotide without the nucleotide analog.

According to aspects of the present disclosure, a blocker oligonucleotide has a $T_m$ in the range of 55° C. to 100° C., such as 60° C. to 100° C., such as 65° C. to 100° C., such as 70° C. to 100° C., such as 75° C. to 99° C., such as 75° C. to 90° C., such as 75° C. to 85° C., such as 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C.

According to aspects of the present disclosure, a set of blocker oligonucleotides has a $T_m$ in the range of 55° C. to 100° C., such as 60° C. to 100° C., such as 65° C. to 100° C., such as 70° C. to 100° C., such as 75° C. to 99° C., such as 75° C. to 90° C., such as 75° C. to 85° C., such as 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C.

According to aspects of the present disclosure, 3' end of one or more of the blocker oligonucleotides is optionally modified to prevent polymerase extension from 3' end, for example, in a post-hybridization capture PCR step. Any of various techniques for modifying the 3' end of one or more blocker oligonucleotides is modified to prevent polymerase extension from the 3' end can be used, including but not limited to, removal or modification of the hydroxyl group at 3' end of an oligonucleotide, such as to include a 3' dideoxy-C (ddC), a phosphate group, or a 3' spacer. According to aspects of the present disclosure, a spacer is present at the 3' terminus of a blocker oligonucleotide. A nonlimiting example is a 3' Spacer C3 (abbreviated 3SpC3), a 3 carbon chain (C3) which is attached to the terminal 3' hydroxyl group of the oligonucleotide blocker. Alternatively, 3' end of the blocker oligonucleotides are not modified to prevent polymerase extension from 3' end, for example if no post-hybridization capture PCR step, or other polymerase-mediated extension step post-hybridization capture, is to be used.

The terms "hybridization" and "hybridized" refer to pairing and binding of complementary nucleic acids. Hybridization occurs to varying extents between two nucleic acids depending on factors such as the degree of complementarity of the nucleic acids, the melting temperature, $T_m$, of the nucleic acids and the stringency of hybridization conditions, and post-hybridization wash conditions, as is well known in the art. The term "stringency of hybridization conditions" refers to conditions of temperature, ionic strength, and composition of a hybridization medium with respect to particular common additives such as formamide, betaine, and polyethylene glycol. The term "stringency of post-hybridization wash conditions" refers to conditions of temperature, ionic strength, and composition of a hybridization medium, although additives such as surfactants, formamide, betaine, and polyethylene glycol are not commonly used in wash conditions. Particular surfactants that can be used include, for example, SDS (sodium dodecyl sulfate), sodium lauroyl sarcosinate (Sarkosyl), and CTAB (cetyltrimethyl-ammonium bromide). Determination of particular hybridization conditions, and post-hybridization wash conditions, relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. High stringency post-hybridization wash conditions are those which only maintain hybridization of substantially complementary nucleic acids. The term "annealing" as used herein refers to the pairing and binding of an oligonucleotide to a target nucleic acid. There is no intended distinction between the terms "annealing" and "hybridizing."

The term "complementary" as used herein encompasses, but is not limited to, Watson-Crick base pairing between nucleotides, between nucleotide analogs, or between nucleotides and nucleotide analogs, wherein nucleotides and/or nucleotide analogs are hydrogen bonded to one another, for example with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA-5' is 100%, or completely, complementary to a region of the nucleotide sequence 5'-TTAGCTGG-3'. The term "complement" as used herein refers to a nucleotide sequence that is complementary to a given nucleotide sequence.

Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize. The terms "specific hybridization" and "specifically hybridizes" refer to hybridization of a particular nucleic acid to a target nucleic acid without substantial hybridization to nucleic acids other than the target nucleic acid in a sample.

The term "palindromic nucleotide sequence" refers to a nucleotide sequence that is an inverted repeat such that the nucleotide sequence is the same whether read in 5' to 3' direction or when read from 5' to 3' on the complementary strand. For instance, a palindromic nucleotide sequence read from 5' to 3' is 5'-GGATCC-3' which is the same when read from 5' to 3' on the complementary strand, i.e. 3'-CCTAGG-5'.

Annealing of blocker oligonucleotides to excess adapters is performed at an annealing temperature. The annealing temperature depends on factors, including the nucleic acid sequence of the blocker oligonucleotides, and the target nucleic acid, and the composition of the reaction medium, including factors such as salt concentration, and concentration of additives, such as but not limited to, formamide, betaine, polyethylene glycol, a surfactant, such as SDS, and DMSO. Typically, the annealing temperature is in the range of 30° C. to 65° C., but can be higher or lower. The annealing temperature may be higher or lower than the blocker oligonucleotide melting temperature ($T_m$), however, typically blocker oligonucleotides according to aspects of the present disclosure have a higher $T_m$ than the annealing temperature to ensure that the blocker oligonucleotides are bound, i.e. hybridized, to their targets during annealing. Similarly, one or more post-hybridization washes may be performed at a temperature which is lower than the $T_m$ of the blocker oligonucleotide(s).

Following annealing of blocker oligonucleotides to excess adapters, a hybridized complex is produced wherein the first blocker oligonucleotide 3' terminus is adjacent to an adenylated 5' end nucleotide of a first unligated 3' adapter and the second blocker oligonucleotide 3' terminus is adjacent to an adenylated 5' end nucleotide of a second unligated 3' adapter, thereby reducing excess unligated 3' adapters.

Optionally, the first blocker oligonucleotide 3' terminus of the hybridized complex is ligated to the adjacent adenylated nucleotide at the 5' terminus of the first unligated 3' adapter and the second blocker oligonucleotide 3' terminus of the hybridized complex is ligated to the adjacent adenylated nucleotide at the 5' terminus of the second unligated 3' adapter, producing ligated complex, thereby reducing excess unligated 3' adapters.

The hybridized complex or the ligated complex can be separated from the desired sequencing library molecules. Separation of the hybridized complex or the ligated complex from the desired sequencing library molecules may be a size-based separation, such as by column-based separation, filter-based separation, gel-based, separation, binding of either the ligated complex or the desired sequencing library molecules to a solid or semi-solid support, followed by separation of the unbound material from the bound material. According to aspects of the present disclosure, the solid support includes magnetic beads.

Amplification of template DNA is achieved using an in vitro amplification method. The terms "amplify, "amplification," and "amplifying" are used to refer generally to a method or technique for copying a template nucleic acid, thereby producing nucleic acids including copies of all or a portion of the template nucleic acid, the produced nucleic acids also termed amplicons. Amplification methods included in embodiments of the present invention are those which include template directed primer extension catalyzed by a nucleic acid polymerase using a pair of primers which flank the target nucleic acid, illustratively including, but not limited to, Polymerase Chain Reaction (PCR), reverse-transcription PCR (RT-PCR). ligation-mediated PCR (LM-PCR), phi-29 PCR, real-time quantitative PCR (qPCR), whole genome amplification, and other nucleic acid amplification methods, for instance, as described in C. W. Dief-fenbach et al., PCR Primer: A Laboratory Manual, Cold Spring Harbor Laboratory Press, 2003; V. Demidov et al., DNA Amplification: Current Technologies and Applications, Taylor & Francis, 2004; and Kroneis, T. (Ed.), Whole Genome Amplification: Methods and Protocols (Methods in Molecular Biology), 2015, Humana Press ISBN-10: 1493929895.

The term "isothermal amplification" refers to nucleic acid amplification that includes single temperature amplification and therefore avoids the need for thermal cycling (as in PCR). Examples of isothermal amplification include, but are not limited to, circular helicase-dependent amplification (cHDA), genome exponential amplification reaction (GEAR), helicase-dependent amplification (HDA), isother-mal multiple displacement amplification (IMDA), loop-mediated isothermal amplification (LAMP), multiple dis-placement amplification (MDA), nicking enzyme amplification reaction (NEAR), nucleic acid sequence-based amplification (NASBA), ramification amplification (RAM), recombinase polymerase amplification (RPA), rolling circle amplification (RCA), self-sustained sequence replication (3SR), signal mediated amplification of RNA technology (SMART), strand-displacement amplification (SDA), single primer isothermal amplification (SPIA), and transcription mediated amplification (TMA).

The terms "amplified nucleic acid," "amplified DNA," and "amplicon," as well as plurals thereof refer to the product of a process of copying a target nucleic acid template.

Amplified nucleic acids optionally contain additional materials such as, but not limited to, nucleic acid sequences, functional groups for chemical reaction and detectable labels, present in the primers and not present in the original nucleic acid template. Non-limiting examples of primer-derived nucleic acid sequences that can be incorporated into amplicons, and thereby incorporated into the library pro-duced, include, universal sequences, adapters, index sequences, identification sequences, detection sequences, sorting sequences, captures sequences, restriction enzyme cleavage sites, sequencing primer binding site sequences, and amplification primer binding site sequences.

The term "universal sequence" refers to a nucleic acid sequence that is present in a plurality of nucleic acid molecules that also contain nucleic acid sequences which are not common to the plurality of nucleic acid molecules. A universal sequence allows the plurality of nucleic acid molecules to share a common functional aspect, such as binding to a particular primer or capture moiety. Non-limiting examples of universal extension primer binding sites include sequences that are identical to or complemen-tary to P5 and P7 primers. P5 and P7 primers, their comple-ments, and uses, such as in flow cells for capture on a flow cells substrate for next generation sequencing (NGS), are known in the art, for example as detailed in WO2015106941.

An index sequence is incorporated into amplicons during library preparation according to aspects of the present dis-closure. An index sequence is a unique nucleic acid sequence common to a set of amplicons, e.g. to identify the set of amplicons as originating from a particular source. Index sequences allow for multiplexing since multiple nucleic acids from different sources can be pooled for sequencing and later can be "demultiplexed" for data analy-sis if desired.

The term "primer" refers to an oligonucleotide that is capable of acting as a site of initiation of synthesis of a template directed primer extension product under conditions in which synthesis of an oligonucleotide primer extension product which is complementary to a template nucleic acid is induced. Such conditions include the presence of nucleo-tides and/or nucleotide analogs, and a suitable polymerase, at a suitable temperature and pH.

A primer is typically about 10-30 contiguous nucleotides in length and may be longer or shorter. An oligonucleotide primer is completely or substantially complementary to a region of a template nucleic acid such that, under hybrid-ization conditions, the oligonucleotide primer anneals to the complementary region of the template nucleic acid. Appro-priate reactions conditions for synthesis of a primer exten-sion product according to aspects of the present disclosure include presence of suitable reaction components including, but not limited to, a polymerase; and nucleotides and/or nucleotide analogs.

Various primers may be used in methods according to aspects of the present disclosure, such as amplification primers, sequencing primers, and primers for reverse tran-scription.

Primer design is well-known to those of skill in the art and are designed according to well-known methods and criteria.

For instance, when using a pair of primers, such as in an amplification reaction, the annealing temperature of the primers should be about the same, within a few degrees. In general, the primers should not form dimers with each other and the primers should not form secondary structures, such as hairpins. Methods and considerations for primer design and amplification procedures are described in detail in Yuryev, A., PCR Primer Design, Methods in Molecular Biology, vol. 42, Human Press, 2007; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Primer extension, producing a first strand complementary DNA, is accomplished using a polymerase enzyme under extension reaction conditions compatible with the polymerase activity to produce a complementary strand. Particular conditions and protocols for primer extension are detailed in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

According to aspects of the present disclosure, the sample nucleic acids are RNA, i.e. sample RNA, and the sample RNA is reverse transcribed, producing cDNA. The sample RNA may be reverse transcribed before or after addition of the adapters.

According to aspects of methods of the present disclosure, the method includes annealing a reverse transcription primer to target nucleic acids including RNA; and reverse transcribing the RNA, producing a first strand complementary DNA (cDNA) which is complementary to the RNA.

Annealing the reverse transcription primer, or reverse transcription primer set, to target nucleic acids is performed at an annealing temperature. The annealing temperature depends on factors, including the nucleic acid sequence of the reverse transcription primer, or primers, and the target nucleic acids, and the composition of the reaction medium, including factors such as salt concentration, and concentration of additives, such as but not limited to, formamide, betaine, polyethylene glycol, SDS, and DMSO. Typically, the annealing temperature is in the range of 30° C. to 65° C., but can be higher or lower. The annealing temperature may be higher or lower than the reverse transcription primer melting temperature (Tm). Often annealing temperatures are higher than the Tm of the reverse transcription primer to improve the stringency of the reaction.

Methods of generating a sequencing library are provided according to the present disclosure which include reverse transcribing target RNA, producing first strand complementary DNA (cDNA), is accomplished using a reverse transcriptase enzyme under reaction conditions compatible with reverse transcriptase enzyme activity to transcribe the target RNA. Particular conditions and protocols for reverse transcription are detailed in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002.

Methods of generating a sequencing library are provided according to the present disclosure which further include polymerizing a second strand of DNA complementary to the first strand cDNA, producing double-stranded cDNA. Polymerizing a second strand of DNA complementary to the first strand cDNA may include providing an appropriate DNA polymerase and polymerizing to produce double-stranded cDNA under reaction conditions compatible with DNA polymerase activity to produce double-stranded cDNA.

Suitable polymerases may include bacterial DNA polymerases, eukaryotic 30 DNA polymerases, archaeal DNA polymerases, viral DNA polymerases, Taq polymerase, DNA polymerase I, T4 DNA polymerase, Pfu polymerase, and phage DNA polymerases, including the Klenow fragment of DNA polymerase I, SEQUENASE 1.0 and SEQUENASE 2.0 (U.S. Biochemical), T5 DNA polymerase, and Phi29 DNA polymerase, among others.

Sequencing of amplicons is accomplished using any of various sequencing methodologies, including, traditional Sanger sequencing and massively parallel sequencing methodologies ("next generation sequencing").

Advantageously, paired end reads are performed. The term "paired end reads" refers to a sequencing technique including one sequencing "read" from each end of an amplicon to be sequenced. This allows for a greater yield of sequencing data and increased confidence in the sequencing results.

According to aspects of the present disclosure, excess unligated 3' adapters are reduced but not eliminated by formation of hybridized complexes or ligation complexes, such that a step of ligating 5' adapter to a library insert, also includes ligating 5' adapter to some of the excess unligated 3' adapter, producing adapter-dimers wherein a 5' adapter is covalently bonded by ligation to a 3' adapter at a 5' adapter-3' adapter interface. Thus, according to aspects of the present disclosure, methods of reducing adapter-dimers in a sequencing library further include inhibiting amplification of the adapter-dimers in an amplification reaction such that the sequencing library molecules are selectively enriched by the amplification reaction compared to the adapter-dimers.

According to aspects of the present disclosure, inhibiting amplification of the adapter-dimers includes removing at least some of the adapter-dimers prior to amplification.

According to aspects of the present disclosure, removing at least some of the adapter-dimers prior to amplification includes one or more of: 1) specific enzymatic cleavage of the adapter-dimers; 2) CRISPR/Cas9-based cleavage of the adapter-dimers; 3) gel purification; 4) SPRI-bead based size selection; and 5) adding an adapter-dimer blocker oligonucleotide to the mixture, the adapter-dimer blocker oligonucleotide effective to inhibit amplification of the adapter-dimers.

Specific enzymatic cleavage of the adapter-dimers refers to use of a restriction endonuclease to cleave the adapter-dimers into two or more fragments, thereby reducing the number of adapter-dimers. The nucleotide sequence of the adapter-dimers can be analyzed to determine which restriction endonuclease(s) will cleave the adapter-dimers or various restriction endonucleases can be assayed to determine which are effective to cleave the adapter-dimers, preventing amplification of the adapter-dimers.

CRISPR/Cas-based cleavage refers to use of a CRISPR/Cas system to cleave the adapter-dimers into two or more fragments, thereby reducing the number of adapter-dimers. According to aspects of the disclosure, the adapter-dimers contain a CRISPR stem loop and the Cas protein recognizes the stem loop, cleaving the adapter-dimers, or binding with high affinity to the stem loop without cleaving the adapter-dimers, thereby preventing amplification of the adapter-dimers.

Solid Phase Reversible Immobilization (SPRI)-bead based size selection can be used to separate adapter-dimers from sequencing library molecules in a mixture, either by immobilizing the adapter-dimers on a solid support and removing the solid support with the immobilized adapter-dimers from the mixture or by immobilizing the sequencing library molecules on a solid support and removing the solid support with the immobilized sequencing library molecules from the mixture, followed by elution of the sequencing library molecules from the solid support.

The term "adapter-dimer blocker oligonucleotide" refers to an oligonucleotide which specifically hybridizes to at least a portion of an adapter-dimer containing an amplification primer binding site, thereby preventing amplification of the adapter-dimer. An adapter-dimer blocker oligonucleotide has a length in the range of about 10 to about 300 nucleotides in length, depending on factors such as the size of the adapter-dimer, and hybridization conditions to be used. According to aspects of the present disclosure, an adapter-dimer blocker oligonucleotide has a length in the range of about 10 to about 300 nucleotides in length, about 10 to about 200 nucleotides in length, about 10 to about 100 nucleotides in length, about 10 to about 75 nucleotides in length, about 10 to about 50 nucleotides in length, about 10 to about 40 nucleotides in length, about 10 to about 30 nucleotides in length, or about 10 to about 20 nucleotides in length. According to aspects of the present disclosure, about 10%, 20%, 30%, 40%, 50%, 60%, 70%, 80%, 90% or more of the nucleotides of the adapter-dimer blocker oligonucleotide are non-naturally occurring nucleotides. According to aspects of the present disclosure, about 10%, 20%, 30%, 40%, 50%, 60%, 70%, 80%, 90% or more of the nucleotides of the adapter-dimer blocker oligonucleotide are $T_m$ increasing nucleotides and/or nucleotide analogs. According to aspects of the present disclosure, about 10%, 20%, 30%, 40%, 50%, 60%, 70%, 80%, 90% or more of the nucleotides of the adapter-dimer blocker oligonucleotide are LNA monomers, PNA monomers, BNA monomers, other $T_m$ increasing nucleotide analogs, or any two or more thereof. According to aspects of the present disclosure, about 10%, 20%, 30%, 40%, 50%, 60%, 70%, 80%, 90% or more of the nucleotides of the adapter-dimer blocker oligonucleotide are LNA monomers.

An example adapter-dimer blocker oligonucleotide is 5'-C+G+AG+AA+T+T+CC+A+GA+T+CG+T+C+G+GA+C+T+G−3' (SEQ ID NO:2), where +'s indicate LNA bases (i.e. incorporated LNA monomers). A 3SpC3 (3' (C3) propyl spacer) is present on 3' end in a preferred example.

Kits for reducing adapter-dimers in a sequencing library are provided according to aspects of the present disclosure which include one or more blocker oligonucleotides and/or pairs of blocker oligonucleotides for reducing adapter-dimers in a sequencing library According to aspects of the present disclosure, kits for reducing adapter-dimers in a sequencing library further include one or more adapter-dimer blocker oligonucleotides effective to block amplification of adapter-dimers.

According to aspects of the present disclosure, kits for reducing adapter-dimers in a sequencing library are provided which include an adapter-dimer blocker oligonucleotide complementary to one or more adjacent portions of the adapter-dimers, the one or more adjacent portions including at least one nucleotide of 5' adapter at 5' adapter-3' adapter interface, and an adjacent portion of 3' adapter including an amplification primer binding site.

A kit according to aspects of the present disclosure includes one or more blocker oligonucleotides and/or one or more adapter-dimer blocker oligonucleotides in aqueous, buffered, or lyophilized form. The one or more blocker oligonucleotides and/or one or more adapter-dimer blocker oligonucleotides may be packaged together or separately. The one or more blocker oligonucleotides and/or one or more adapter-dimer blocker oligonucleotides may be aliquoted into suitable amounts for use in sequencing library preparation, or may be packaged in bulk for aliquoting by a user. Additional kit components may include, but are not limited to, buffers, diluents, stabilizers, preservatives, reagents such as nucleotides, nucleotide analogs, and enzymes.

Compositions and methods according to aspects of the present disclosure have utility in numerous applications, including, but not limited to, reducing adapter-dimers sequenced in sequencing protocols, particularly in sequencing libraries including small inserts.

Compositions and methods according to aspects of the present disclosure provide high sensitivity such that rare nucleic acids present in a sample can be detected more often. Reliable detection of rare nucleic acids allows for diagnostic and therapeutic methods of analyzing nucleic acids in a patient sample.

Embodiments of inventive compositions and methods are illustrated in the following examples. These examples are provided for illustrative purposes and are not considered limitations on the scope of inventive compositions and methods.

EXAMPLES

Example 1

3' adapter ligation
  a. Combine the following components on ice:
    i. 1 μL input RNA (1 ng/μL)
    ii. 9.5 μL Nuclease-free water
    iii. 1 μL 5 uM 3' adapter C3/5rApp/TGGAAT-TCTCGGGTGCCAAGG/3SpC3/ (SEQ ID NO: 3)
    iv. 7 μL 3' ligation buffer
    v. 1.5 μL 3' ligation enzyme mix
    vi. 20 μL total reaction volume
  b. Incubate as follows:
    i. 1 hr at 25° C.
    ii. Hold at 4° C.
Inactivation of unligated 3' adapter
  a. On ice, add 1 μL 10 uM oligonucleotide blocker with a palindromic 3' end to the reaction and mix until homogenous 5'-CACCCGAGAATTCCAC/iisodG//iMe-isodC//iisodG//iMe-isodC/G-3' (SEQ ID NO: 1). Note that in this example the palindromic 3' end of the oligonucleotide blocker allows 3' portions of two oligonucleotide blocker molecules to hybridize with each other, and 5' portion of the blocker oligonucleotides hybridize with the excess 3' adapter, under hybridization conditions, forming a hybridization complex.
  b. Incubate as follows:
    i. 10 min at 70° C.
    ii. Hold at 4° C.
5' adapter ligation
  a. Combine the following components on ice:
    i. 21 μL reaction from previous step
    ii. 1.5 μL 2.5 uM 5' adapter 5'-rGrUrUrCrArGrArGrUrUrCrUrArCrArGrUrCrCrGrArCrGrAr UrC-3' (SEQ ID NO:4)-Note that "r" is used here to emphasize that the nucleotides shown are ribonucleotides.
    iii. 1.5 μL 10 mM ATP (NEB cat #P0756L)
    iv. 2 μL 5' Ligation Enzyme Mix
    v. 26 μL total reaction volume b. Incubate as follows:
    i. 1 hr at 20° C.
    ii. Hold at 4° C.

Reverse transcription a. Start with the 26 µL 5' ligation reaction from the previous step on the thermal cycler.

b. Program a thermal cycler as follows:
    i. 2 min at 70° C.
    ii. 30 min at 50° C.
    iii. 5 min at 90° C.
    iv. Hold at 4° C.

c. Prepare the RT master mix as follows:
    i. 13 µL RT Buffer
    ii. 1 µL 25 UM RT primer 5'-CCTTGGCACCCGAGAATTCCA-3' (SEQ ID NO: 5)
    iii. 2 µL EnzScript Reverse Transcriptase (Enzymatics)
    iv. 16 µL total vol.

d. With the 26 µL mixture from a. in 5' adapter ligation section above on the thermal cycler, start the program.

e. After the thermal cycler has ramped down to 50° C., add and mix 16 µL of the RT master mix on the thermal cycler. Do not remove reaction from thermal cycler.

f. Allow incubation to complete and ramp down to 4° C.

Bead cleanup a. Add and mix 40 µL Adapter Depletion Solution b. Add and mix 40 µL NEXTFLEX Cleanup Beads c. Add and mix 90 µL isopropanol d. Incubate 5 min at room temperature e. Place on magnetic stand for 5 minutes or until solution is clear f. Aspirate to remove the supernatant g. Wash by adding 200 µL 80% ethanol, incubating 30 sec, and aspirating to remove supernatant h. Repeat above step for a total of 2 washes i. Let dry on magnetic stand for a total of 3 minutes. After 1 min, aspirate and remove any liquid that has collected at the bottom of the well j. Remove from magnetic stand and resuspend in 40 µL of Nuclease-free water k. Incubate for 2 minutes l. Place on magnetic stand m. Once beads have formed a pellet, take 18 µL and add to strip tubes. This clean cDNA is saved as a backup.

n. Take another 18 µL and move to a new well. This cDNA will be amplified in the following step.

PCR a. Combine the following components on ice:
    i. 18 µL cDNA from previous step 5n
    ii. 2 µL NEXTFLEX UDI Barcoded Primer Mix
    iii. 5 µL NEXTFLEX PCR Master Mix
    iv. 1 µL 10 µM long dblock02C3 (or water) 5'-C+G+AG+AA+T+T+CC+A+GA+T+CG+T+C+G+GA+C+T+G/3SpC3/(SEQ ID NO:2)
    v. 26 µL total reaction volume b. Incubate reaction as follows:
    i. 30 sec at 98° C.
    ii. 10 sec at 98° C.
    iii. 20 sec at 65° C. Repeat for a total of 22 cycles
    iv. 15 sec at 72° C.
    v. 2 min at 72° C.
    vi. Hold at 4° C.

Bead cleanup a. Take 25 µL of the PCR reaction from the previous step b. Add and mix 48.6 µL NEXTFLEX Cleanup Beads c. Incubate 5 min at room temperature d. Place on magnetic stand for 5 minutes or until solution is clear e. Aspirate to remove the supernatant f. Wash by adding 200 µL 80% ethanol, incubating 30 sec, and aspirating to remove supernatant g. Repeat above step for a total of 2 washes h. Let dry on magnetic stand for a total of 3 minutes. After 1 min, aspirate and remove any liquid that has collected at the bottom of the well i. Remove from magnetic stand and resuspend in 20 µL of Nuclease-free water j. Incubate for 2 minutes k. Place on magnetic stand l. Once beads have formed a pellet, remove 18 µL. This is your sequencing library.

Sequencing Parameters (MiSeq)

a. 2% phiX b. 1×76

Figure 3:
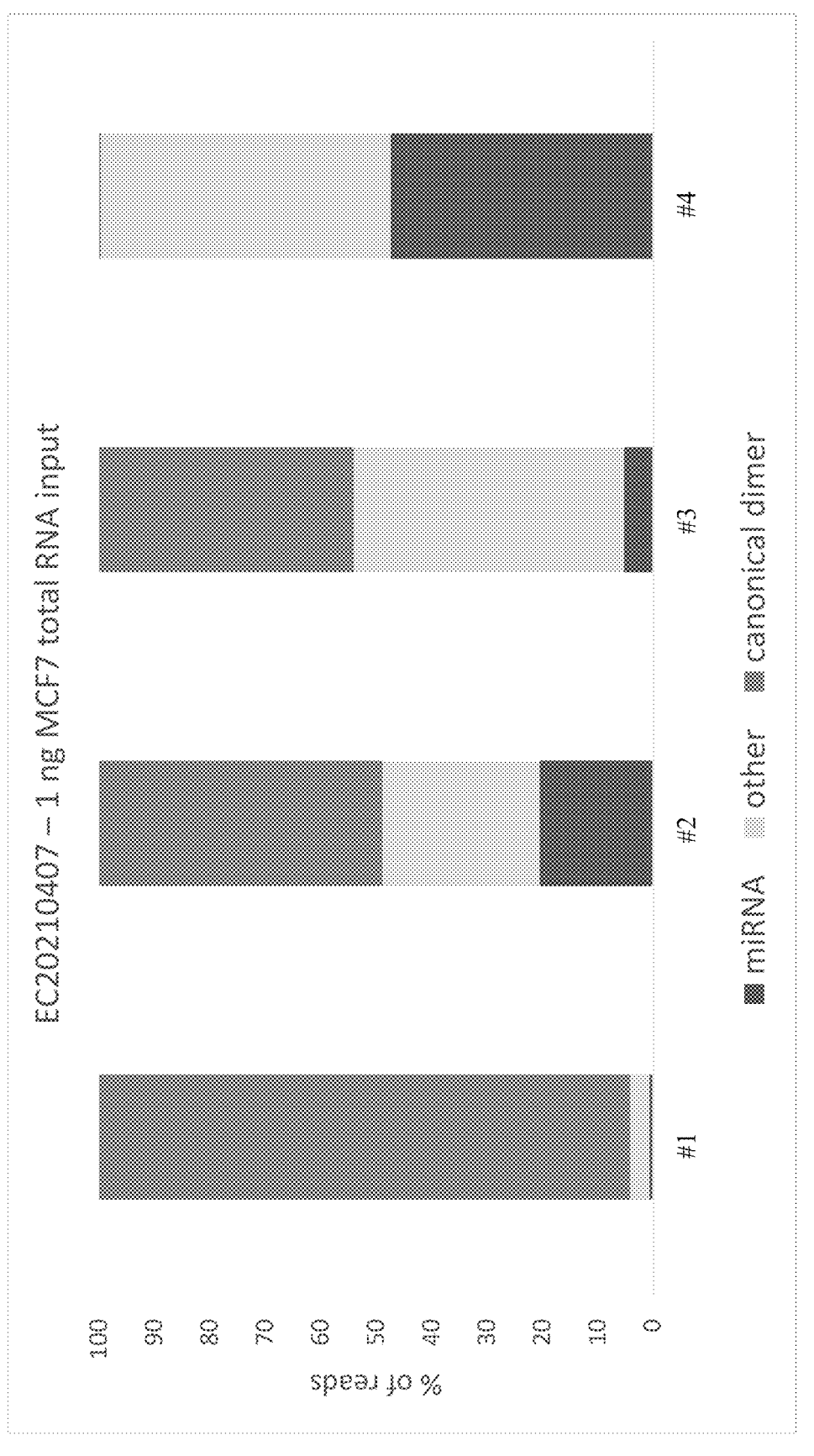
FIG. 3 is a graph showing inhibition of adapter-dimer formation according to aspects of the present disclosure.

Results are shown in FIG. 3.

Example 2

1. 3' Adapter Ligation a. Combine the following components on ice:
    i. "X" µL input RNA (1 ng Total RNA)
    ii. 1 µL tRNA/YRNA Blockers
    ii. "Y" µL Nuclease-free water
    iv. 1 µL 3' Adenylated Adapter 5'-rApp/TGGAATTCTCGGGTGCCAAGG/3SpC3/-3' (SEQ ID NO:3)
    v. 12.5 µL 3' Ligation Buffer
    vi. 1.5 µL 3' Ligation Enzyme Mix
    vii. 20 µL total reaction volume (Water and RNA should equal 4 µL total volume)
    viii. Mix viscous reaction by vortexing for at least 3 seconds until homogenized.

c. Incubate as follows:
    i. 1 hr at 25° C.
    ii. Hold at 4° C.

2. Inactivation of unligated 3' adapter a. On ice, add 4 µL Adapter Inactivation Mix including an oligonucleotide blocker with a palindromic 3' end: 5'-CACCCGAGAATTCCAC/iisodG//iMe-isodC//iisodG//iMe-isodC/G-3' (SEQ ID NO:1), to the reaction and mix until homogenous.

b. Incubate as follows:
    i. 2 min at 70° C.
    ii. Hold at 4° C. (reaction should turn yellow)

3. 5' Adapter Ligation a. Combine the following components on ice:
    i. 24 µL reaction from previous step
    ii. 1 µL 5' Adapter 5'-UCUUUCCCUACACGACG-CUCUUCCGAUCU-3' (SEQ ID NO: 6)
    iii. 3 µL 5' Ligation Buffer
    iv. 2 µL 5' Ligation Enzyme Mix
    v. 30 µL TOTAL reaction volume b. Incubate as follows:
    i. 1 hr at 20° C.
    ii. Hold at 4° C.
       (reaction should turn orange)

Figure 4:
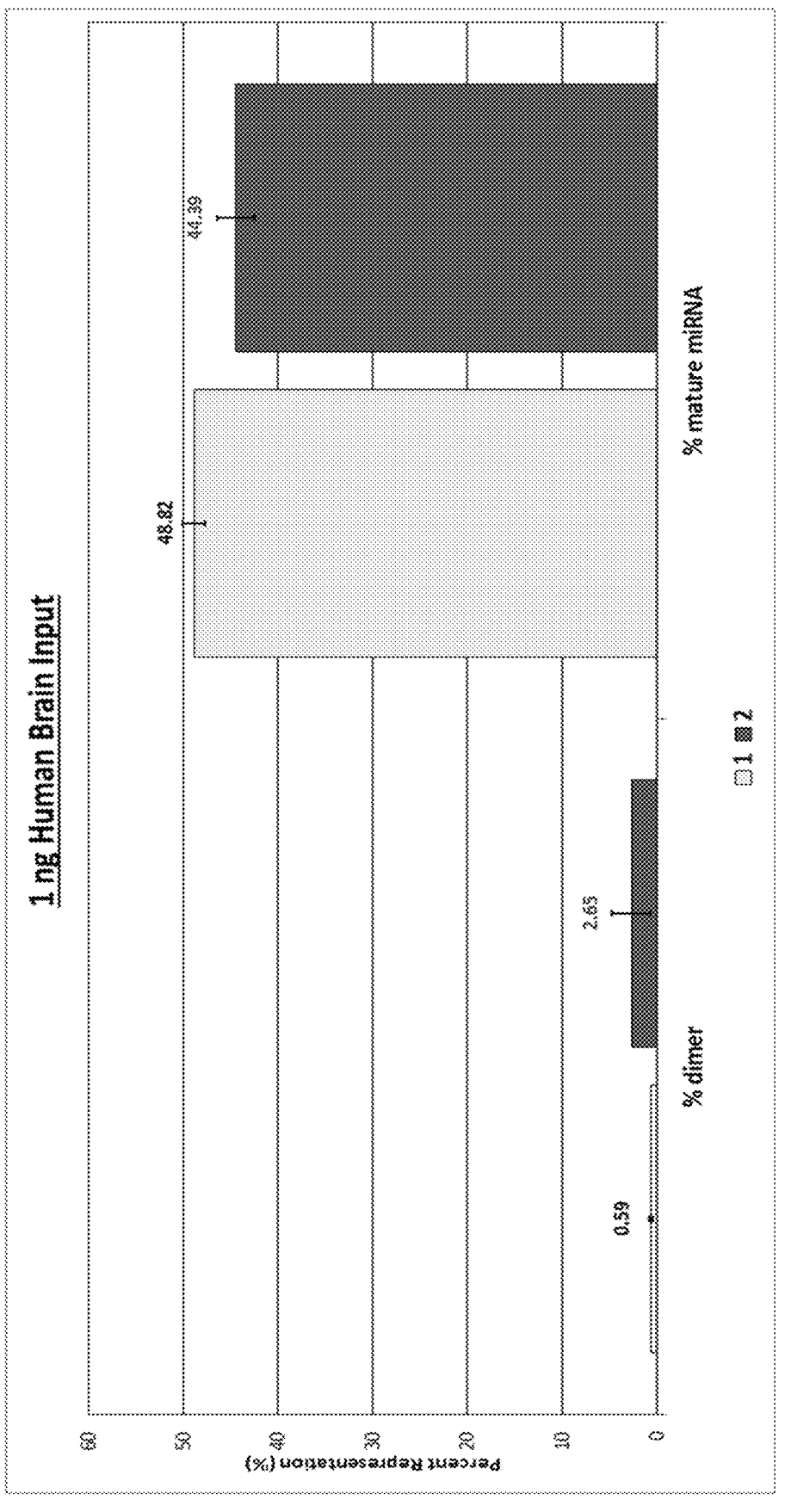
FIG. 4 is a graph showing results demonstrating a significant decrease in the percent dimer sequenced, compared to a conventional method, due to a significant decrease in the percent adapter dimer incorporated into the sequencing library using a method including use of one or more blocker oligonucleotides according to aspects of the present disclosure. Further shown is an increased percent of mature miRNA sequenced, compared to a conventional method, due to a significant decrease in the percent adapter dimer incorporated into the sequencing library using a method including use of one or more blocker oligonucleotides according to aspects of the present disclosure.
Figure 5:
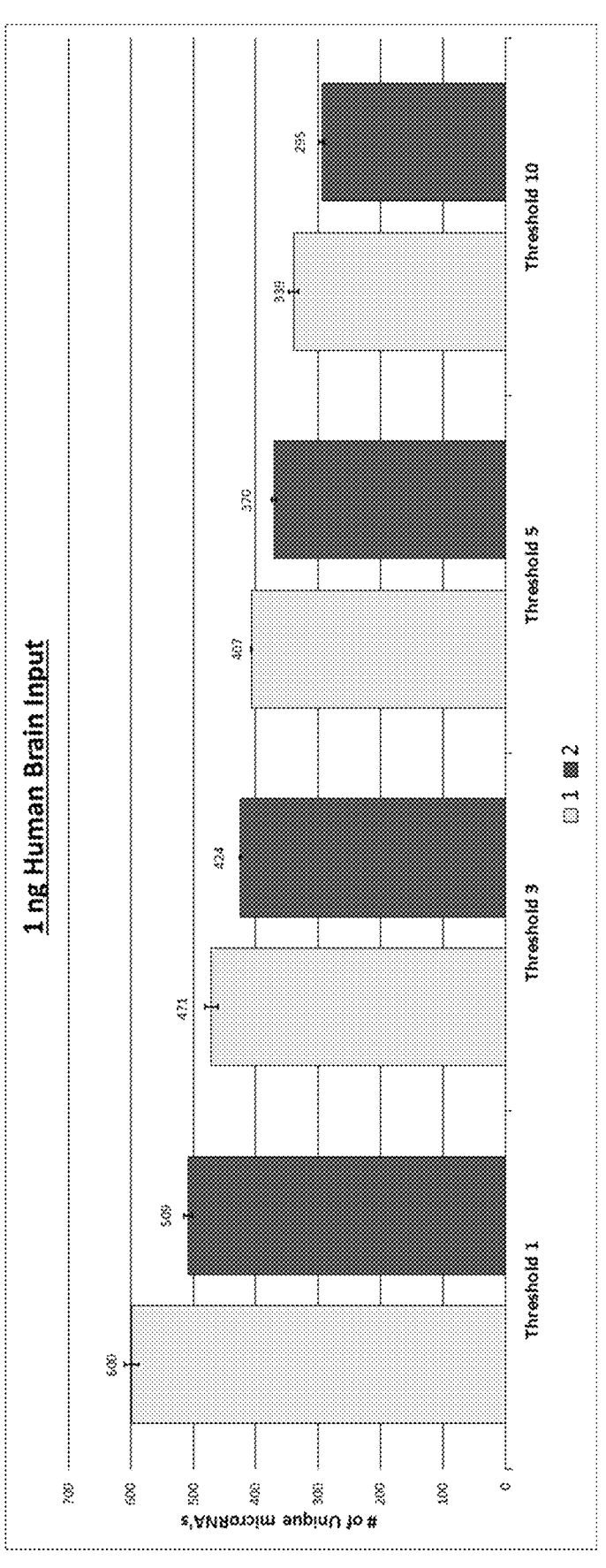
FIG. 5 is a graph showing results obtained using a method including use of one or more blocker oligonucleotides according to aspects of the present disclosure and the dark gray bars, 2, represent data obtained using a conventional method. The results show a comparison of the number of unique miRNAs represented in the sequencing data, i.e. 600 unique single sequences found at least once using a method including one or more blocker oligonucleotides according to aspects of the present disclosure compared to only 509 unique single sequences found at least once using a conventional method; 471 unique sequences found at least 3 times using a method including one or more blocker oligonucleotides according to aspects of the present disclosure compared to only 424 unique single sequences found at least three times using a conventional method; 407 unique single sequences found at least 5 times using a method including one or more blocker oligonucleotides according to aspects of the present disclosure compared to only 370 unique single sequences found at least 5 times using a conventional method; and 339 unique single sequences found at least 10 times using a method including one or more blocker oligonucleotides according to aspects of the present disclosure compared to only 295 unique single sequences found at least 10 times using a conventional method.
Figure 6:
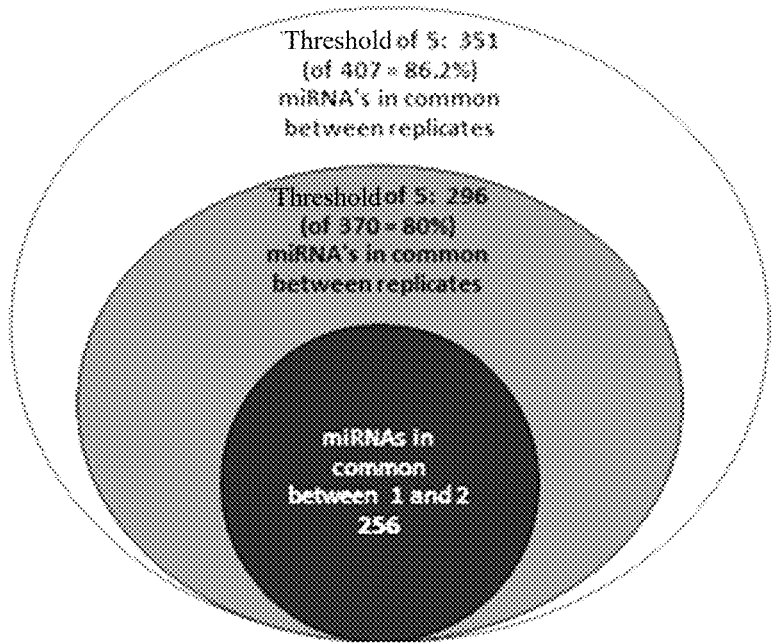
FIG. 6 is a Venn diagram showing a comparison of the number of unique miRNAs found with a threshold of 5 that are the same between 3 replicates using a method including use of one or more blocker oligonucleotides according to aspects of the present disclosure (large gray circle) and 3 replicates obtained using a conventional method (medium sized medium gray circle). The smallest black circle represents the number of unique miRNAs common to both methods.

4. Reverse Transcription
   a. Combine the following components on ice:
      i. 7 μL RT Buffer
      iii. 2 μL RT Enzyme Mix
      iv. 1 μL 25 uM RT primer
         5'-CCTTGGCACCCGAGAATTCCA-3' (SEQ ID
         NO: 5)
      v. 40 μL total reaction volume
   b. Incubate as follows:
      ii. 60 min at 50° C.
      iii. 5 min at 90° C.
      iv. Hold at 4° C.
   c. Allow incubation to complete and ramp down to 4° C.
5. Bead cleanup
   a. Add and mix 40 μL Adapter Depletion Solution
   b. Add and mix 40 μL NEXTFLEX Cleanup Beads
   c. Add and mix 90 μL isopropanol
   d. Incubate 5 min at room temperature
   e. Place on magnetic stand for 5 minutes or until
      solution is clear
   f. Aspirate to remove the supernatant
   g. Wash by adding 200 μL 80% ethanol, incubating 30
      sec, and aspirating to remove supernatant
   h. Repeat above step for a total of 2 washes
   i. Let dry on magnetic stand for a total of 3 minutes.
      After 1 min, aspirate and remove any liquid that has
      collected at the bottom of the well
   j. Remove from magnetic stand and resuspend in 18 μL
      of Nuclease-free water
   k. Incubate for 2 minutes
   l. Place on magnetic stand
   m. Take 16 μL and move to a new well. This cDNA will
      be amplified in the following step.
6. PCR
   a. Combine the following components on ice:
      i. 16 μL cDNA from previous step m from the Bead
         Cleanup section above
      ii. 4 μL RNA UDI Barcoded Primer Mix 12.5 μM
      iii. 6 μL NEXTFLEX Small RNA PCR Master Mix
      iv. 26 μL Total reaction volume
   Incubate reaction as follows:
      i. 30 sec at 98° C.
      ii. 10 sec at 98° C.
      iii. 20 sec at 65° C.
      iv. 15 sec at 72° C.
         Repeat ii, iii, and iv for a total of 22 cycles
      v. 2 min at 72° C.
      vi. Hold at 4° C.
7. Dual-sided Bead cleanup
   a. Take 26 μL of the PCR reaction from the previous
      step
   b. Add and mix 34 μL NEXTFLEX Cleanup Beads
   c. Incubate 5 min at room temperature
   d. Transfer 56 μL of supernatant to a new well
   e. Add and mix 13 μL NEXTFLEX Cleanup Beads
   d. Place on magnetic stand for 5 minutes or until
      solution is clear
   e. Aspirate to remove the supernatant
   f. Wash by adding 200 μL 80% ethanol, incubating 30
      sec, and aspirating to remove supernatant
   g. Repeat above step for a total of 2 washes
   h. Let dry on magnetic stand for a total of 3 minutes.
      After 1 min, aspirate and remove any liquid that has
      collected at the bottom of the well
   i. Remove from magnetic stand and resuspend in 17 μL
      of Nuclease-free water
   j. Incubate for 2 minutes k. Place on magnetic stand
   l. Once beads have formed a pellet, remove 15 μL. This
      is your sequencing library.
8. Sequencing Parameters (MiSeq)
   a. 2% phiX
   b. 1×75
Results are shown in FIG. 4.
Items
   Item 1. A method of reducing adapter-dimers in a sequencing library, comprising: combining sample nucleic acids, each having a 5' end and a 3' end, with 3' adapters each having a 5' end portion at least 8 nucleotides in length and a 5' terminus which is an adenylated nucleotide, and a ligase, in a mixture under ligation reaction conditions, producing 1) first ligation products each comprising 3' end of a sample nucleic acid ligated to the 5' terminus of a 3' adapter, and 2) excess unligated, 3' adapters in the mixture;
   adding blocker oligonucleotides to the mixture, the blocker oligonucleotides comprising:
   a) a first blocker oligonucleotide comprising:
   i) a first blocker oligonucleotide 5' portion at least 8 nucleotides in length and ii) a first blocker oligonucleotide 3' portion at least 1 to 20 nucleotides in length and comprising a first oligonucleotide 3' terminus, wherein at least 1 of the 1 to 20 nucleotides is a non-naturally occurring nucleotide analog; and
   b) a second blocker oligonucleotide comprising:
   iii) a second oligonucleotide 5' portion at least 8 nucleotides in length and iv) a second blocker oligonucleotide 3' portion at least 1 to 20 nucleotides in length and comprising a second blocker oligonucleotide 3' terminus, wherein at least 1 of the 1 to 20 nucleotides is a non-naturally occurring nucleotide analog;
   wherein the first blocker oligonucleotide 3' portion and the second blocker oligonucleotide 3' portion are equal in length and complementary to each other;
   wherein the first blocker oligonucleotide 5' portion and the second blocker oligonucleotide 5' portion are both complementary to 5' end portion of 3' adapters;
   incubating the mixture under hybridization conditions, thereby hybridizing the first blocker oligonucleotide 3' portion with the second blocker oligonucleotide 3' portion, hybridizing the first blocker oligonucleotide 5' portion with the excess unligated 3' adapters, and thereby hybridizing the second blocker oligonucleotide 5' portion with the excess unligated 3' adapters, producing a hybridized complex wherein the first blocker oligonucleotide 3' terminus is adjacent to an adenylated 5' end nucleotide of a first unligated 3' adapter and the second blocker oligonucleotide 3' terminus is adjacent to an adenylated 5' end nucleotide of a second unligated 3' adapter; thereby reducing excess unligated 3' adapters in the mixture, producing a purified mixture.
   Item 2. The method of item 1, wherein the first blocker oligonucleotide 3' terminus and the second blocker oligonucleotide 3' terminus are both capable of being ligated to the adenylated nucleotide at the 5' terminus of the excess unligated 3' adapters; and further comprising ligating the first blocker oligonucleotide 3' terminus of the hybridized complex to the adjacent adenylated nucleotide at the 5' terminus of the first unligated 3' adapter and ligating the second blocker oligonucleotide 3' terminus of the hybridized complex to the adjacent adenylated nucleotide at the 5' terminus of the second unligated 3' adapter, producing ligated complex, thereby reducing excess unligated 3' adapters in the mixture, producing a purified mixture.

Item 3. The method of item 1 or 2, wherein 2, 3, 4, 5, 6, 7, 8, 9, 10, 11, 12, 13, 14, 15, 16, 17, 18, 19, or 20 of the at least 1 to 20 nucleotides of the first blocker oligonucleotide 3' portion are non-naturally occurring nucleotide analogs and 2, 3, 4, 5, 6, 7, 8, 9, 10, 11, 12, 13, 14, 15, 16, 17, 18, 19, or 20 of the at least 1 to 20 nucleotides of the second blocker oligonucleotide 3' portion are non-naturally occurring nucleotide analogs.

Item 4. The method of any one of item 1, 2, or 3, wherein when the first blocker oligonucleotide 3' portion and the second blocker oligonucleotide 3' portion are each 2, 3, 4, 5, 6, 7, 8, 9, 10, 11, 12, 13, 14, 15, 16, 17, 18, 19, or 20 nucleotides in length, the first blocker oligonucleotide 3' portion and the second blocker oligonucleotide 3' portion each comprise a palindromic nucleotide sequence, wherein the palindromic nucleotide sequence of the first blocker oligonucleotide 3' portion is identical to the palindromic nucleotide sequence of the second blocker oligonucleotide 3' portion.

Item 5. The method of any one of items 1 to 4, further comprising: adding 5' adapter to the mixture, 5' adapter having a 3' terminus, wherein the first ligation products each comprise 3' end of a sample nucleic acid ligated to the 5' terminus of a 3' adapter, and 5' end of a sample nucleic acid ligated to the 3' terminus of a 5' adapter, thereby producing sequencing library molecules, the sequencing library molecules comprising a sample nucleic acid insert disposed between, and bonded to, a 5' adapter and a 3' adapter.

Item 6. The method of any one of items 1 to 5, further comprising: adding 5' adapter to the purified mixture; and incubating the purified mixture under ligation reaction conditions, thereby 1) ligating 5' adapter to the first ligation product, producing sequencing library molecules, the sequencing library molecules comprising a sample nucleic acid insert disposed between, and bonded to, a 5' adapter and a 3' adapter.

Item 7. The method of any one of items 1 to 6, wherein excess unligated 3' adapters are reduced but not eliminated such that the ligating includes ligating 5' adapter to at least some of the excess unligated 3' adapter, producing adapter-dimers comprising a 5' adapter bonded to a 3' adapter at a 5' adapter-3' adapter interface; and further comprising inhibiting amplification of the adapter-dimers in an amplification reaction such that the sequencing library molecules are selectively enriched by the amplification reaction compared to the adapter-dimers.

Item 8. The method of any one of items 1 to 7, wherein inhibiting amplification of the adapter-dimers comprises removing at least some of the adapter-dimers prior to amplification.

Item 9. The method of item 7 or item 8, wherein inhibiting amplification of the adapter-dimers comprises one or more of: specific enzymatic cleavage of the adapter-dimers; CRISPR/Cas9-based cleavage of the adapter-dimers; gel purification; SPRI-bead based size selection; and adding an adapter-dimer blocker oligonucleotide to the mixture, the adapter-dimer blocker oligonucleotide effective to inhibit amplification of the adapter-dimers.

Item 10. The method of item 9, wherein the adapter-dimer blocker oligonucleotide is complementary to one or more adjacent portions of the adapter-dimers, the one or more adjacent portions comprising at least one nucleotide of 5' adapter at 5' adapter-3' adapter interface, and an adjacent portion of 3' adapter comprising an amplification primer binding site.

Item 11. The method of any one of items 1 to 10, wherein the first blocker oligonucleotide and the second blocker oligonucleotide have the same nucleotide sequence.

Item 12. The method of item 1, wherein the sample nucleic acids are, or include, RNA, and further comprising reverse transcribing the RNA, producing reverse transcribed sequencing library molecules.

Item 13. The method of item 1, wherein the sample nucleic acids are, or include, DNA.

Item 14. The method of item 12 or 13, further comprising amplifying the sequencing library molecules.

Item 15. A pair of oligonucleotides for reducing adapter-dimers in a sequencing library, comprising:
a) a first blocker oligonucleotide comprising:
i) a first blocker oligonucleotide 5' portion at least 8 nucleotides in length and ii) a first blocker oligonucleotide 3' portion at least 1 to 20 nucleotides in length and comprising a first oligonucleotide 3' terminus, wherein at least 1 of the 1 to 20 nucleotides is a non-naturally occurring nucleotide analog; and
b) a second blocker oligonucleotide comprising:
iii) a second oligonucleotide 5' portion at least 8 nucleotides in length and iv) a second blocker oligonucleotide 3' portion at least 1 to 20 nucleotides in length and comprising a second blocker oligonucleotide 3' terminus, wherein at least 1 of the 1 to 20 nucleotides is a non-naturally occurring nucleotide analog;
wherein the first blocker oligonucleotide 3' portion and the second blocker oligonucleotide 3' portion are equal in length and complementary to each other; and
wherein the first blocker oligonucleotide 5' portion and the second blocker oligonucleotide 5' portion are both complementary to 5' end portion of 3' adapters.

Item 16. The pair of oligonucleotides for reducing adapter-dimers in a sequencing library of item 15, wherein the first blocker oligonucleotide 3' terminus and the second blocker oligonucleotide 3' terminus are both capable of being ligated to the adenylated nucleotide at the 5' terminus of the excess unligated 3' adapters.

Item 17. The pair of oligonucleotides for reducing adapter-dimers in a sequencing library of item 15 or 16, wherein 2, 3, 4, 5, 6, 7, 8, 9, 10, 11, 12, 13, 14, 15, 16, 17, 18, 19, or 20 of the at least 1 to 20 nucleotides of the first blocker oligonucleotide 3' portion are non-naturally occurring nucleotide analogs and 2, 3, 4, 5, 6, 7, 8, 9, 10, 11, 12, 13, 14, 15, 16, 17, 18, 19, or 20 of the at least 1 to 20 nucleotides of the second blocker oligonucleotide 3' portion are non-naturally occurring nucleotide analogs.

Item 18. The pair of oligonucleotides for reducing adapter-dimers in a sequencing library of any one of items 15, 16, or 17, wherein when the first blocker oligonucleotide 3' portion and the second blocker oligonucleotide 3' portion are each 2, 3, 4, 5, 6, 7, 8, 9, 10, 11, 12, 13, 14, 15, 16, 17, 18, 19, or 20 nucleotides in length, the first blocker oligonucleotide 3' portion and the second blocker oligonucleotide 3' portion each comprise a palindromic nucleotide sequence, wherein the palindromic nucleotide sequence of the first blocker oligonucleotide 3' portion is identical to the palindromic nucleotide sequence of the second blocker oligonucleotide 3' portion.

Item 19. The pair of oligonucleotides for reducing adapter-dimers in a sequencing library of any one of items 15 to 18, wherein the first blocker oligonucleotide and the second blocker oligonucleotide each have a length in the range of about 11 to about 50 nucleotides.

Item 20. The pair of oligonucleotides for reducing adapter-dimers in a sequencing library of any one of items 15 to 19, wherein the first blocker oligonucleotide and the second blocker oligonucleotide have the same nucleotide sequence.

Item 21. A kit for reducing adapter-dimers in a sequencing library, comprising the pair of oligonucleotides of any one of items 15 to 20.

Item 22. The kit of item 21, further comprising an adapter-dimer blocker oligonucleotide effective to block amplification of adapter-dimers.

Item 23. The kit of item 22, wherein the adapter-dimer blocker oligonucleotide is complementary to one or more adjacent portions of the adapter-dimers, the one or more adjacent portions comprising at least one nucleotide of 5' adapter at 5' adapter-3' adapter interface, and an adjacent portion of 3' adapter comprising an amplification primer binding site.

Item 24. The method of any one of items 1 to 14 or the kit of any one of items 21 to 23 wherein the first blocker and the second blocker have identical nucleic acid sequences.

Item 25. The method of any one of items 1 to 14 or the kit of any one of items 21 to 24 wherein the first blocker and the second blocker have different nucleic acid sequences.

Item 26. A method, kit, or pair of oligonucleotides substantially as shown or described herein.

Item 27. The method of any one of items 1 to 14, wherein the first blocker oligonucleotide and the second blocker oligonucleotide each have a length in the range of about 11 to about 50 nucleotides.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. A method of reducing adapter-dimers in a sequencing library, comprising:

combining sample nucleic acids, each having a 5' end and a 3' end, with 3' adapters each having a 5' end portion at least 8 nucleotides in length and a 5' terminus which is an adenylated nucleotide, and a ligase, in a mixture under ligation reaction conditions, producing 1) first ligation products each comprising 3' end of a sample nucleic acid ligated to the 5' terminus of a 3' adapter, and 2) excess unligated, 3' adapters in the mixture;

adding blocker oligonucleotides to the mixture, the blocker oligonucleotides comprising:

a) a first blocker oligonucleotide comprising:

i) a first blocker oligonucleotide 5' portion at least 8 nucleotides in length and ii) a first blocker oligonucleotide 3' portion at least 1 to 20 nucleotides in length and comprising a first oligonucleotide 3' terminus, wherein at least 1 of the 1 to 20 nucleotides is a non-naturally occurring nucleotide analog; and b) a second blocker oligonucleotide comprising:

iii) a second oligonucleotide 5' portion at least 8 nucleotides in length and iv) a second blocker oligonucleotide 3' portion at least 1 to 20 nucleotides in length and comprising a second blocker oligonucleotide 3' terminus, wherein at least 1 of the 1 to 20 nucleotides is a non-naturally occurring nucleotide analog;

wherein the first blocker oligonucleotide 3' portion and the second blocker oligonucleotide 3' portion are equal in length and complementary to each other;

wherein the first blocker oligonucleotide 5' portion and the second blocker oligonucleotide 5' portion are both complementary to 5' end portion of 3' adapters;

incubating the mixture under hybridization conditions, thereby hybridizing the first blocker oligonucleotide 3' portion with the second blocker oligonucleotide 3' portion, hybridizing the first blocker oligonucleotide 5' portion with the excess unligated 3' adapters, and thereby hybridizing the second blocker oligonucleotide 5' portion with the excess unligated 3' adapters, producing a hybridized complex wherein the first blocker oligonucleotide 3' terminus is adjacent to an adenylated 5' end nucleotide of a first unligated 3' adapter and the second blocker oligonucleotide 3' terminus is adjacent to an adenylated 5' end nucleotide of a second unligated 3' adapter; thereby reducing excess unligated 3' adapters in the mixture, producing a purified mixture.

2. The method of claim 1, wherein the first blocker oligonucleotide 3' terminus and the second blocker oligonucleotide 3' terminus are both capable of being ligated to the adenylated nucleotide at the 5' terminus of the excess unligated 3' adapters; and further comprising ligating the first blocker oligonucleotide 3' terminus of the hybridized complex to the adjacent adenylated nucleotide at the 5' terminus of the first unligated 3' adapter and ligating the second blocker oligonucleotide 3' terminus of the hybridized complex to the adjacent adenylated nucleotide at the 5' terminus of the second unligated 3' adapter, producing ligated complex, thereby reducing excess unligated 3' adapters in the mixture, producing a purified mixture.

3. The method of claim 1, wherein 2, 3, 4, 5, 6, 7, 8, 9, 10, 11, 12, 13, 14, 15, 16, 17, 18, 19, or 20 of the at least 1 to 20 nucleotides of the first blocker oligonucleotide 3' portion are non-naturally occurring nucleotide analogs and 2, 3, 4, 5, 6, 7, 8, 9, 10, 11, 12, 13, 14, 15, 16, 17, 18, 19, or 20 of the at least 1 to 20 nucleotides of the second blocker oligonucleotide 3' portion are non-naturally occurring nucleotide analogs.

4. The method of claim 1, wherein when the first blocker oligonucleotide 3' portion and the second blocker oligonucleotide 3' portion are each 2, 3, 4, 5, 6, 7, 8, 9, 10, 11, 12, 13, 14, 15, 16, 17, 18, 19, or 20 nucleotides in length, the first blocker oligonucleotide 3' portion and the second blocker oligonucleotide 3' portion each comprise a palindromic nucleotide sequence, wherein the palindromic nucleotide sequence of the first blocker oligonucleotide 3' portion is identical to the palindromic nucleotide sequence of the second blocker oligonucleotide 3' portion.

5. The method of claim 1, further comprising: adding 5' adapter to the mixture, the 5' adapter having a 3' terminus, wherein the first ligation products each comprise 3' end of a sample nucleic acid ligated to the 5' terminus of a 3' adapter, and 5' end of a sample nucleic acid ligated to the 3' terminus of a 5' adapter, thereby producing sequencing library molecules, the sequencing library molecules comprising a sample nucleic acid insert disposed between, and bonded to, a 5' adapter and a 3' adapter.

6. The method of claim 1, further comprising: adding 5' adapter to the purified mixture; and incubating the purified mixture under ligation reaction conditions, thereby 1) ligating the 5' adapter to the first ligation product, producing sequencing library molecules, the sequencing library molecules comprising a sample nucleic acid insert disposed between, and bonded to, a 5' adapter and a 3' adapter.

7. The method of claim 6, wherein excess unligated 3' adapters are reduced but not eliminated such that the ligating includes ligating 5' adapter to at least some of the excess unligated 3' adapter, producing adapter-dimers comprising a 5' adapter bonded to a 3' adapter at a 5' adapter-3' adapter interface; and further comprising inhibiting amplification of the adapter-dimers in an amplification reaction such that the sequencing library molecules are selectively enriched by the amplification reaction compared to the adapter-dimers.

8. The method of claim 7, wherein inhibiting amplification of the adapter-dimers comprises removing at least some of the adapter-dimers prior to amplification.

9. The method of claim 7, wherein inhibiting amplification of the adapter-dimers comprises one or more of: specific enzymatic cleavage of the adapter-dimers; CRISPR/Cas9-based cleavage of the adapter-dimers; gel purification; SPRI-bead based size selection; and adding an adapter-dimer blocker oligonucleotide to the mixture, the adapter-dimer blocker oligonucleotide effective to inhibit amplification of the adapter-dimers.

10. The method of claim 9, wherein the adapter-dimer blocker oligonucleotide is complementary to one or more adjacent portions of the adapter-dimers, the one or more adjacent portions comprising at least one nucleotide of 5' adapter at 5' adapter-3' adapter interface, and an adjacent portion of 3' adapter comprising an amplification primer binding site.

11. The method of claim 1, wherein the first blocker oligonucleotide and the second blocker oligonucleotide have the same nucleotide sequence.

12. The method of claim 1, wherein the sample nucleic acids are, or include, RNA, and further comprising reverse transcribing the RNA, producing reverse transcribed sequencing library molecules.

13. The method of claim 1, wherein the sample nucleic acids are, or include, DNA.

14. The method of claim 12, further comprising amplifying the sequencing library molecules.

* * * * *